United States Patent
Graef et al.

(10) Patent No.: US 7,166,190 B2
(45) Date of Patent: Jan. 23, 2007

(54) METHODS FOR FORMING A FLUTED COMPOSITE

(75) Inventors: Peter A. Graef, Puyallup, WA (US); Clifford R. Bolstad, Federal Way, WA (US); Fred B. Howard, Gig Harbor, WA (US); Charles E. Miller, Kent, WA (US); Daniel T. Bunker, Karhula (FI)

(73) Assignee: National Institute for Strategic Technology Acquisistion and Commercialization, Manhattan, KS (US)

( * ) Notice: Subject to any disclaimer, the term of this patent is extended or adjusted under 35 U.S.C. 154(b) by 0 days.

(21) Appl. No.: 11/067,857

(22) Filed: Feb. 28, 2005

(65) Prior Publication Data

US 2006/0005934 A1  Jan. 12, 2006

Related U.S. Application Data

(63) Continuation of application No. 10/679,835, filed on Oct. 6, 2003, now abandoned, which is a continuation of application No. 09/664,576, filed on Sep. 18, 2000, now Pat. No. 6,630,054, which is a continuation of application No. PCT/US99/05997, filed on Mar. 18, 1999.

(60) Provisional application No. 60/111,845, filed on Dec. 11, 1998, provisional application No. 60/082,790, filed on Apr. 23, 1998, provisional application No. 60/082,771, filed on Apr. 23, 1998, provisional application No. 60/078,779, filed on Mar. 19, 1998.

(51) Int. Cl.
  *D21H 23/14* (2006.01)
  *D21H 13/02* (2006.01)
(52) U.S. Cl. .................. 162/184; 162/157.6; 162/123; 162/146; 162/101; 162/9

(58) Field of Classification Search .................. 162/9, 162/157.6, 141, 146, 183, 101, 123, 125, 162/127, 132–133, 158, 164.1, 168.1, 184; 241/21, 24.1, 24.11, 24.19, 24.29, 28; 604/367–368, 604/358, 385.01
See application file for complete search history.

(56) References Cited

U.S. PATENT DOCUMENTS

| 3,716,449 A | 2/1973 | Gatward et al. |
| 3,756,913 A | 9/1973 | Wodka |
| 3,783,872 A * | 1/1974 | King .......................... 604/368 |

(Continued)

FOREIGN PATENT DOCUMENTS

EP         251673        1/1988

(Continued)

OTHER PUBLICATIONS

Kouris, Michael, "Dictionary of Paper," 1996, TAPPI Press, 5th Edition, p. 248.

*Primary Examiner*—José A. Fortuna
(74) *Attorney, Agent, or Firm*—Hovey Williams LLP

(57) ABSTRACT

Methods for forming an absorbent fibrous composite containing absorbent material dispersed in bands through the composite and along the composite's length are disclosed. The methods generally include depositing a fibrous slurry on a foraminous support to form a web and depositing or injecting absorbent material into the web across its width to provide a web having absorbent material in bands along the composite's length. Drying the web provides a fluted absorbent composite. In one embodiment, the method is a wetlaid method and in another embodiment, the method is a foam-forming method. Preferably, the methods are twin-wire forming methods.

19 Claims, 23 Drawing Sheets

U.S. PATENT DOCUMENTS

| | | | |
|---|---|---|---|
| 3,819,470 A | 6/1974 | Shaw et al. | |
| 3,868,287 A | 2/1975 | Lewyckyj | |
| 3,871,952 A | 3/1975 | Robertson | |
| 3,897,784 A | 8/1975 | Fitzgerald | |
| 3,938,782 A | 2/1976 | Robertson | |
| 4,174,417 A | 11/1979 | Rydell | |
| 4,204,054 A | 5/1980 | Lesas et al. | |
| 4,256,111 A | 3/1981 | Lassen | |
| 4,270,977 A | 6/1981 | Herman et al. | |
| 4,354,901 A | 10/1982 | Kopolow | |
| 4,364,992 A | 12/1982 | Ito et al. | |
| 4,443,297 A | 4/1984 | Cheshire et al. | |
| 4,551,142 A | 11/1985 | Kopolow | |
| 4,559,050 A | 12/1985 | Iskra | |
| 4,568,341 A | 2/1986 | Mitchell et al. | |
| 4,605,401 A | 8/1986 | Chmelir et al. | |
| 4,610,678 A * | 9/1986 | Weisman et al. | 604/368 |
| 4,685,914 A | 8/1987 | Holtman | |
| 4,704,116 A | 11/1987 | Enloe | |
| 4,798,603 A | 1/1989 | Meyer et al. | |
| 4,885,204 A | 12/1989 | Bither et al. | |
| 4,888,093 A | 12/1989 | Dean et al. | |
| 4,889,596 A | 12/1989 | Schoggen et al. | |
| 4,935,022 A * | 6/1990 | Lash et al. | 604/368 |
| 4,988,344 A | 1/1991 | Reising et al. | |
| 4,988,345 A | 1/1991 | Reising | |
| 5,061,259 A | 10/1991 | Goldman et al. | |
| 5,102,597 A | 4/1992 | Roe et al. | |
| 5,134,007 A | 7/1992 | Reising et al. | |
| 5,137,537 A | 8/1992 | Herron et al. | |
| 5,147,343 A | 9/1992 | Kellenberger | |
| 5,147,345 A * | 9/1992 | Young et al. | 604/378 |
| 5,149,335 A | 9/1992 | Kellenberger et al. | |
| 5,215,627 A | 6/1993 | Willis et al. | |
| 5,217,445 A | 6/1993 | Young et al. | |
| 5,277,915 A | 1/1994 | Provonchee et al. | |
| 5,281,207 A | 1/1994 | Chmielewski et al. | |
| 5,284,610 A | 2/1994 | Tai | |
| 5,324,561 A | 6/1994 | Rezai et al. | |
| 5,330,822 A | 7/1994 | Berg et al. | |
| 5,334,176 A * | 8/1994 | Buenger et al. | 604/367 |
| 5,350,370 A | 9/1994 | Jackson et al. | |
| 5,354,290 A | 10/1994 | Gross | |
| 5,360,420 A | 11/1994 | Cook et al. | |
| 5,364,382 A | 11/1994 | Latimer et al. | |
| 5,372,877 A | 12/1994 | Kannenkeril | |
| 5,415,643 A | 5/1995 | Kolb | |
| 5,422,169 A | 6/1995 | Roe | |
| 5,425,725 A | 6/1995 | Tanzer et al. | |
| 5,429,629 A | 7/1995 | Latimer et al. | |
| 5,486,167 A | 1/1996 | Dragoo et al. | |
| 5,505,718 A | 4/1996 | Roe et al. | |
| 5,509,915 A | 4/1996 | Hanson et al. | |
| 5,522,810 A | 6/1996 | Allen, Jr. et al. | |
| H1565 H | 7/1996 | Brodof et al. | |
| 5,531,728 A | 7/1996 | Lash | |
| 5,562,646 A | 10/1996 | Goldman et al. | |
| 5,597,873 A | 1/1997 | Chambers et al. | |
| 5,599,335 A | 2/1997 | Goldman et al. | |
| 5,601,542 A | 2/1997 | Melius et al. | |
| 5,607,550 A | 3/1997 | Akers | |
| 5,637,105 A | 6/1997 | Tanaka et al. | |
| 5,651,862 A | 7/1997 | Anderson et al. | |
| 5,653,702 A | 8/1997 | Brohammer et al. | |
| 5,669,894 A | 9/1997 | Goldman et al. | |
| 5,698,078 A | 12/1997 | Mizukami et al. | |
| 5,733,273 A | 3/1998 | Ahr | |
| 5,736,219 A | 4/1998 | Suehr et al. | |
| 5,741,400 A | 4/1998 | Kwak | |
| 5,749,863 A * | 5/1998 | Payne | 604/376 |
| 5,785,696 A | 7/1998 | Inoue et al. | |
| 5,788,684 A | 8/1998 | Abuto et al. | |
| 5,792,129 A | 8/1998 | Johansson et al. | |
| 5,792,513 A | 8/1998 | Koslow | |
| 5,795,439 A | 8/1998 | Euripides et al. | |
| 5,821,179 A | 10/1998 | Masaki et al. | |
| 5,830,202 A | 11/1998 | Bogdanski et al. | |
| 5,836,929 A | 11/1998 | Bewick-Sonntag et al. | |
| 5,843,059 A | 12/1998 | Niemeyer et al. | |
| 5,843,063 A | 12/1998 | Anderson et al. | |
| 5,843,575 A | 12/1998 | Wang et al. | |
| 5,843,852 A | 12/1998 | Dutkiewicz et al. | |
| 5,849,000 A | 12/1998 | Anjur et al. | |
| 5,849,405 A | 12/1998 | Wang et al. | |
| 5,851,672 A | 12/1998 | Wang et al. | |
| 5,853,867 A | 12/1998 | Harada et al. | |
| 5,855,572 A | 1/1999 | Schmidt | |
| 5,858,535 A | 1/1999 | Wang et al. | |
| 5,868,724 A | 2/1999 | Dierckes, Jr. et al. | |
| 5,873,867 A | 2/1999 | Coles et al. | |
| 5,876,979 A | 3/1999 | Andrews et al. | |
| 5,891,120 A | 4/1999 | Chmielewski | |
| 5,895,379 A | 4/1999 | Litchholt et al. | |
| 5,906,894 A | 5/1999 | West et al. | |
| 5,925,439 A | 7/1999 | Haubach | |
| 5,941,862 A | 8/1999 | Haynes et al. | |
| 5,941,863 A | 8/1999 | Guidotti et al. | |
| 5,972,487 A | 10/1999 | Duenk et al. | |
| 5,977,014 A | 11/1999 | Plischke et al. | |
| 6,015,608 A | 1/2000 | Koslow | |
| 6,019,871 A | 2/2000 | Rokman et al. | |
| 6,074,524 A | 6/2000 | Wu et al. | |
| 6,080,909 A | 6/2000 | Osterdahl et al. | |
| 6,086,950 A | 7/2000 | Masaki et al. | |
| 6,129,717 A | 10/2000 | Fujioka et al. | |
| 6,177,605 B1 | 1/2001 | Trombetta et al. | |
| 6,261,679 B1 * | 7/2001 | Chen et al. | 428/317.9 |
| 6,294,710 B1 * | 9/2001 | Schmidt et al. | 604/378 |
| 6,436,231 B1 * | 8/2002 | Graef et al. | 162/9 |
| 6,630,054 B1 * | 10/2003 | Graef et al. | 162/101 |
| 6,969,781 B1 * | 11/2005 | Graef et al. | 604/367 |
| 2003/0009141 A1 * | 1/2003 | Graef et al. | 604/368 |
| 2004/0065420 A1 | 4/2004 | Graef et al. | |

FOREIGN PATENT DOCUMENTS

| | | |
|---|---|---|
| EP | 0339461 | 2/1989 |
| EP | 0528248 | 2/1993 |
| EP | 0437816 | 7/1995 |
| EP | 0685212 | 12/1995 |
| EP | 0719531 | 3/1996 |
| EP | 0528248 | 10/1996 |
| EP | 748894 | 12/1996 |
| EP | 0217666 | 4/1997 |
| GB | 2060018 | 4/1981 |
| GB | 2120696 | 7/1983 |
| GB | 2254255 | 7/1992 |
| GB | 2284831 | 6/1995 |
| GB | 2301362 | 4/1996 |
| JP | 9156012 | 6/1997 |
| WO | WO9306804 | 4/1993 |
| WO | WO9513778 | 5/1995 |
| WO | WO9705839 | 2/1997 |
| WO | WO9718783 | 5/1997 |
| WO | WO9721453 | 6/1997 |
| WO | WO9824392 | 6/1998 |
| WO | WO9837846 | 9/1998 |
| WO | WO9847455 | 10/1998 |
| WO | WO9932721 | 7/1999 |
| WO | WO9947094 | 9/1999 |
| WO | WO0041882 | 7/2000 |
| WO | WO0047153 | 8/2000 |

* cited by examiner

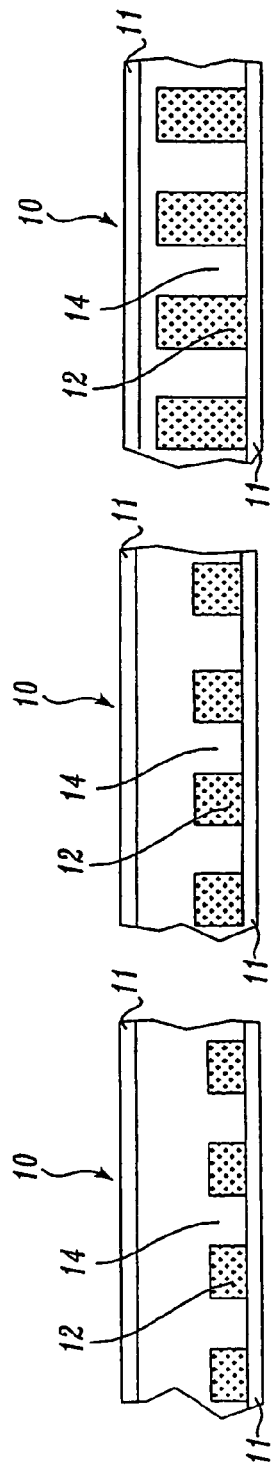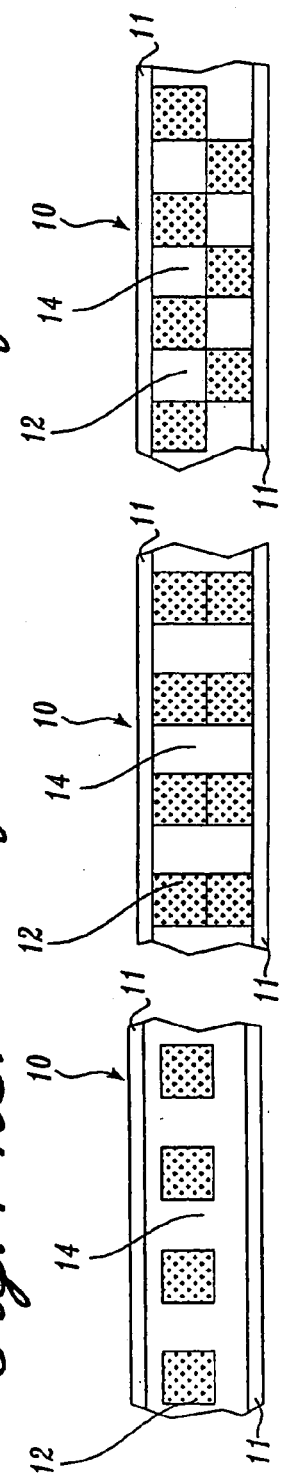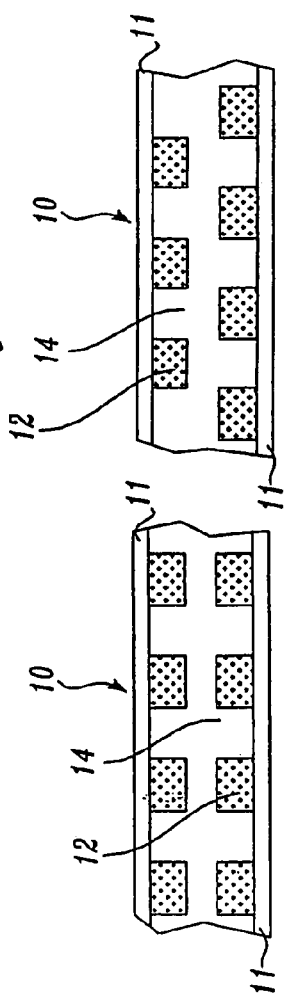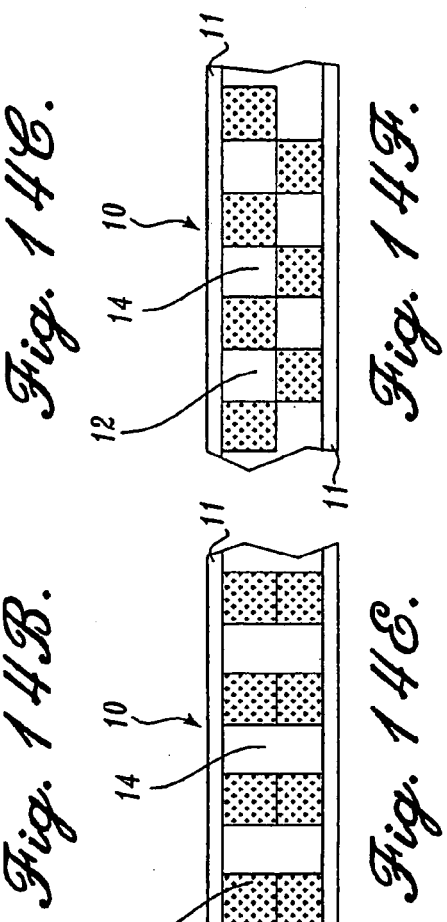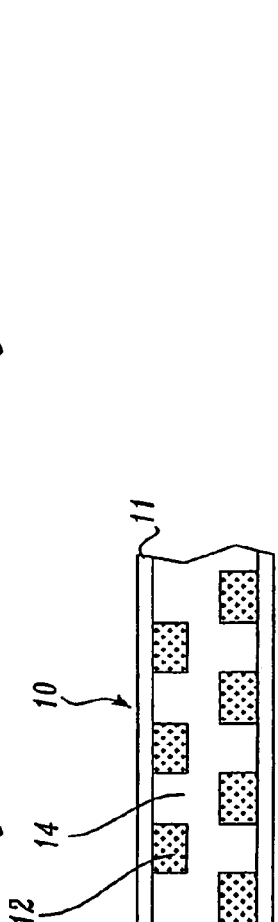

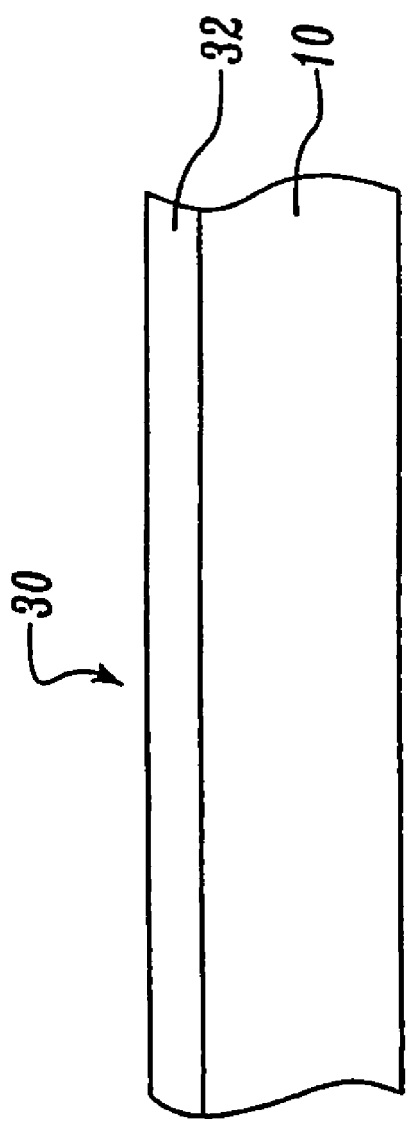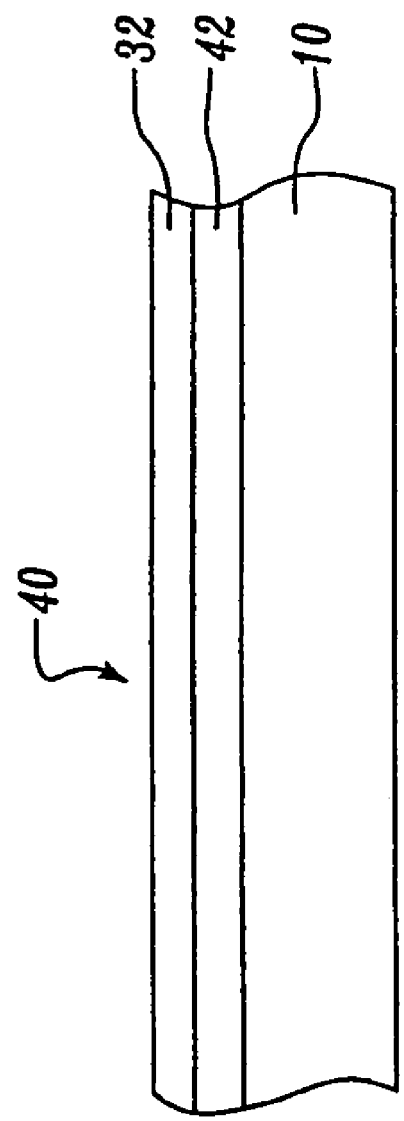

METHODS FOR FORMING A FLUTED COMPOSITE

CROSS-REFERENCE TO RELATED APPLICATIONS

This application is a continuation of U.S. patent application Ser. No. 10/679,835, filed Oct. 6, 2003, now abandoned, which is a continuation of U.S. patent application Ser. No. 09/664,576, filed Sep. 18, 2000, now U.S. Pat. No. 6,630,054, which is a continuation of International Application No. PCT/US99/05997, filed Mar. 18, 1999, which claims the benefit of U.S. Provisional Application No. 60/078,779, filed Mar. 19, 1998, U.S. Provisional Application No. 60/082,771, filed Apr. 23, 1998, U.S. Provisional Application No. 60/082,790, filed Apr. 23, 1998, and U.S. Provisional Application No. 60/111,845, filed Dec. 11, 1998, the benefit of the priority of the filing dates of which are hereby claimed under 35 U.S.C. §§120 and 119, respectively. Each of the applications is incorporated herein by reference in its entirety.

FIELD OF THE INVENTION

The present invention relates to methods for forming an absorbent composite and, more particularly, to methods for forming a fluted absorbent composite that includes superabsorbent material.

BACKGROUND OF THE INVENTION

Cellulose fibers derived from wood pulp are used in a variety of absorbent articles, for example, diapers, incontinence products, and feminine hygiene products. It is desirable for the absorbent articles to have a high absorbent capacity for liquid, rapid liquid acquisition, low rewet, as well as to have good dry and wet strength characteristics for durability in use and effective fluid management. The absorbent capacity of articles made from cellulose fibers is often enhanced by the addition of absorbent materials, such as superabsorbent polymers. Superabsorbent polymers known in the art have the capability to absorb liquids in quantities from 5 to 100 times or more their weight. Thus, the presence of superabsorbent polymers greatly increases the liquid holding capacity of absorbent articles made from cellulose.

Because superabsorbent polymers absorb liquid and swell upon contact with liquid, superabsorbent polymers have heretofore been incorporated primarily in cellulose mats that are produced by the conventional dry, air-laid methods. Wet-laid processes for forming cellulose mats have not been used commercially because superabsorbent polymers tend to absorb liquid and swell during formation of the absorbent mats, thus requiring significant energy for their complete drying.

Cellulose structures formed by the wet-laid process typically exhibit certain properties that are superior to those of an air-laid structure. The integrity, fluid distribution, and the wicking characteristics of wet-laid cellulosic structures are typically superior to those of air-laid structures. Attempts to combine the advantages of wet-laid composites with the high absorbent capacity of superabsorbent materials has led to the formation of various wet-laid absorbent composites that include superabsorbent polymers. These structures can be generally characterized as structures that either have superabsorbent polymers distributed on the surface of a wet-laid composite, laminates, or, alternatively, structures that have superabsorbent material distributed relatively uniformly throughout the composite.

However, absorbent composites that contain superabsorbent materials commonly suffer from gel blocking. Upon liquid absorption, superabsorbent materials tend to coalesce and form a gelatinous mass which prevents the wicking of liquid to unwetted portions of the composite. By preventing distribution of acquired liquid from a composite's unwetted portions, gel blocking precludes the effective and efficient use of superabsorbent materials in fibrous composites. The wicking capacity of conventional fibrous composites that include relatively homogeneous distributions of superabsorbent material is generally significantly restricted after initial liquid insult. The diminished capacity of such fibrous composites results from narrowing of capillary acquisition and distribution channels that accompanies superabsorbent material swelling. The diminution of absorbent capacity and concomitant loss of capillary distribution channels for conventional absorbent cores that include superabsorbent material is manifested by decreased liquid acquisition rates and far from ideal liquid distribution on successive liquid insults.

Accordingly, there exists a need for methods for forming an absorbent composite that includes superabsorbent material and that effectively acquires and wicks liquid throughout the composite and distributes the acquired liquid to absorbent material where the liquid is efficiently absorbed and retained without gel blocking. The present invention seeks to fulfill these needs and provides further related advantages.

SUMMARY OF THE INVENTION

The present invention provides methods for forming an absorbent fibrous composite containing absorbent material dispersed in bands through the composite and along the composite's length. The methods generally include depositing a fibrous slurry on a foraminous support to form a web and depositing or injecting absorbent material to the web across the its width to provide a web having absorbent material in bands along the composite's length. Drying the web provides a fluted absorbent composite. In one embodiment, the method is a wet-laid method and in another embodiment, the method is a foam-forming method. Preferably, the methods are twin-wire forming methods.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 14A–14H are cross-sectional views of representative composites formed in accordance with the present invention;

FIG. 18 is a cross-sectional view of a portion of a component of an absorbent article incorporating a representative composite formed in accordance with the present invention;

FIG. 19 is a cross-sectional view of a portion of a component of an absorbent article incorporating a representative composite formed in accordance with the present invention;

DETAILED DESCRIPTION OF THE PREFERRED EMBODIMENT

Figure 1:
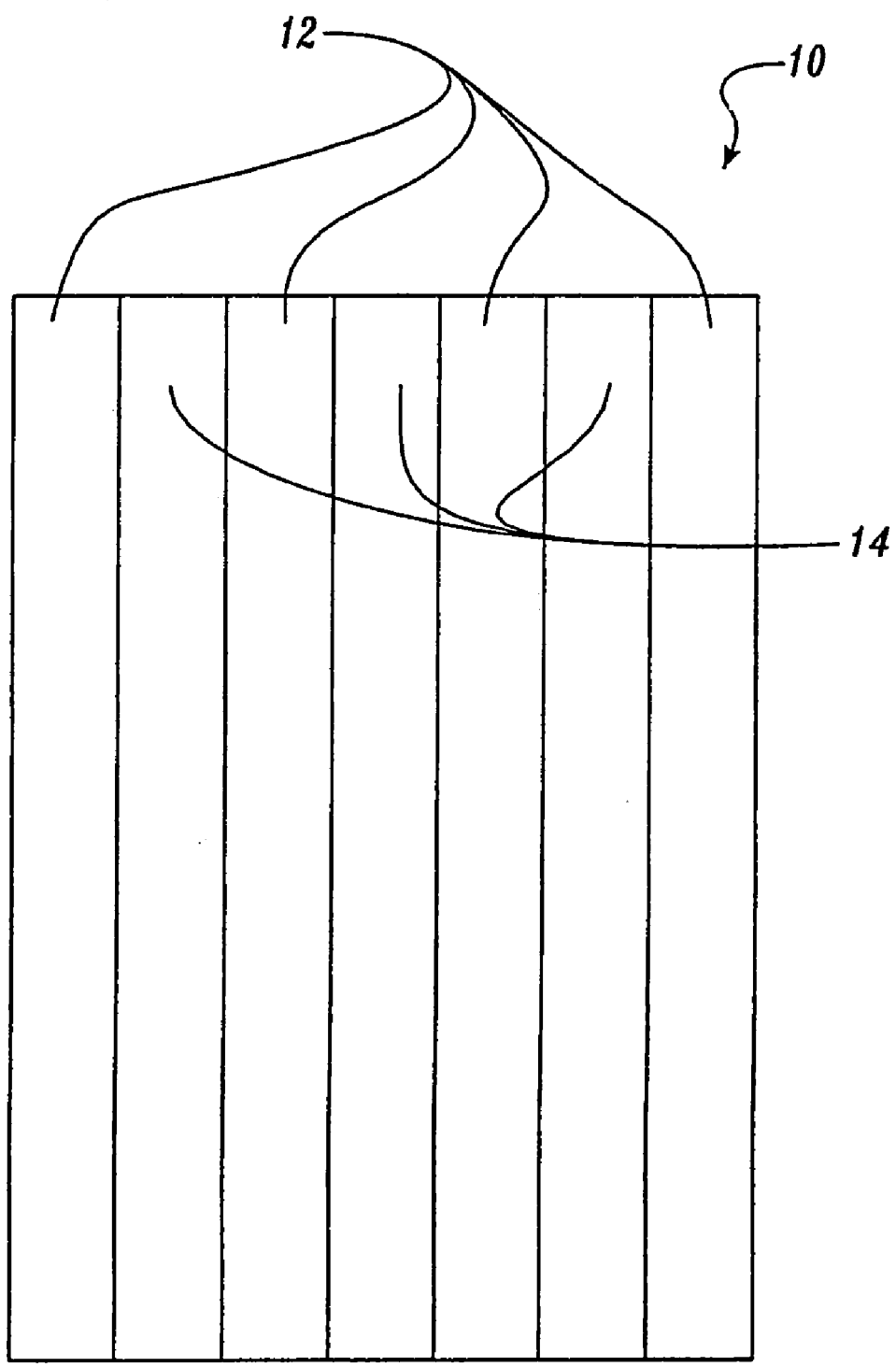
FIG. 1 is a top view of a representative composite formed in accordance with the present invention.

The present invention provides methods for forming an absorbent composite that is a fibrous composite that includes absorbent material. The absorbent composite includes a fibrous matrix having absorbent material dispersed in bands along the composite's length. Between the composite's bands of absorbent material lie distribution zones composed primarily of fibers. Generally, the absorbent material serves to absorb and retain liquid acquired by the composite. The composite's fibrous distribution zones serve to acquire liquid contacting the composite and to distribute the acquired liquid throughout the composite and, ultimately, to the absorbent material.

The absorbent composite can be advantageously incorporated into a variety of absorbent articles such as diapers including disposable diapers and training pants; feminine care products including sanitary napkins, and pant liners; adult incontinence products; toweling; surgical and dental sponges; bandages; food tray pads; and the like. Because the composite is highly absorbent, the composite can be included into an absorbent article as a liquid storage core. In such a construct, the composite can be combined with one or more other composites or layers including, for example, an acquisition and/or a distribution layer. Alternatively, because the composite can rapidly acquire, distribute, and store liquid, the composite can be effectively incorporated into an absorbent article as the sole absorbent component without including other individual layers such as acquisition and/or distribution layers. An absorbent article, such as a diaper, can be formed from a fluted absorbent composite having a liquid pervious facing sheet and a liquid impervious backing sheet. In addition, because of the composite's capacity to rapidly acquire and distribute liquid, the composite can serve as a liquid management layer that acquires and transfers a portion of the acquired liquid to an underlying storage core. Thus, the absorbent composite can be combined with a storage core to provide an absorbent core that is useful in absorbent articles.

The absorbent composite is a fluted composite. As used herein, the term "fluted" refers to the nature of the composite, which on wetting, develops ridges or flutes as a result of absorbent material expansion. As noted above, absorbent material is located in bands or stripes positioned across the composite's width and extending in bands along the composite's length. On contact with liquid acquired by the fibrous composite, absorbent material swelling occurs and produces a wetted composite having ridges or flutes that include swollen absorbent material separated by distribution zones or channels, regions of the composite that are generally substantially free of absorbent material.

The fluted composite is a fibrous structure prepared from cellulosic fibers that have been wetted during the formation process and, as a result, provide a fibrous composite in which the fibers are bonded. As used in this context, the term "bonded" refers to hydrogen bonding that occurs between fibers that have been wetted and then formed into a mat or web. The bonding that occurs between wetted fibers subsequently formed into a fibrous web results in a web that has increased strength and structural integrity, when both wet and dry, compared to air-laid webs. Fibrous webs formed from wetted fibers have strength and integrity significantly greater than air-laid fibrous webs formed from dry fibers, which are incapable of any significant interfiber bonding. The mere proximity of dry fibers in a fibrous web is insufficient to provide any significant bonding between fibers. Consequently, as is well know, air-laid fibrous webs generally lack wet or dry strength. In addition to standard wet-laid processes, wetted fibers can be produced and formed into fibrous webs by foam-forming processes.

Figure 2A:
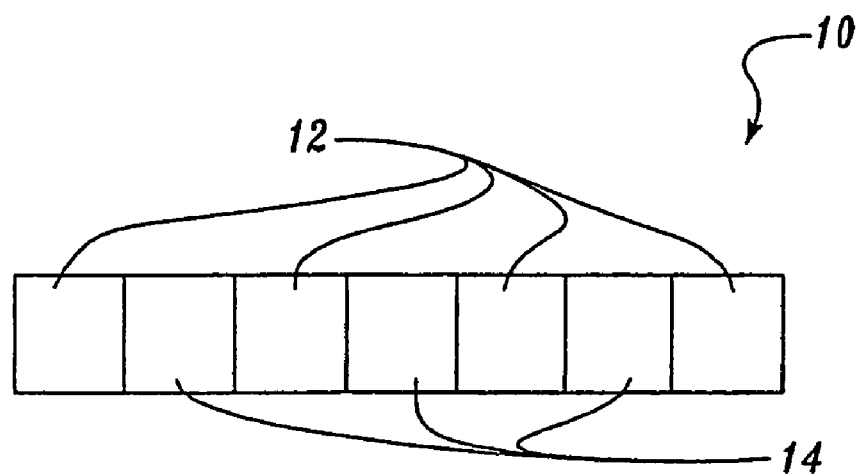
FIG. 2A is a cross-sectional view of a representative composite of the present invention in a dry state.
Figure 2B:
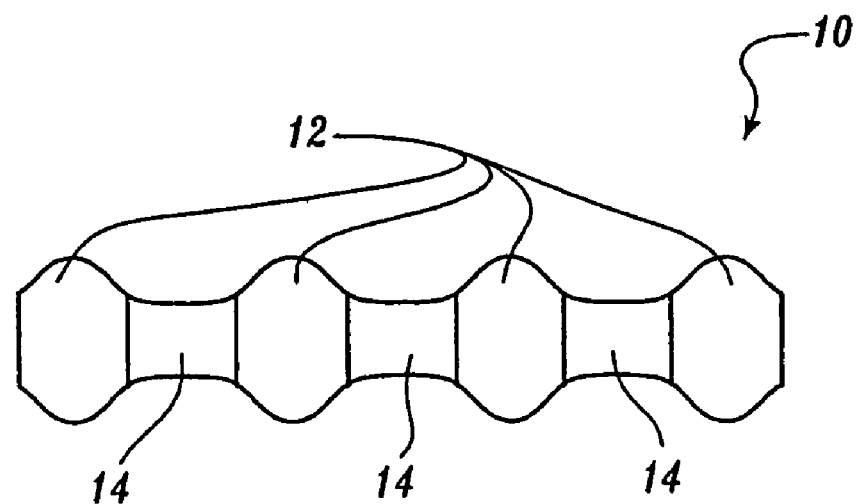
FIG. 2B is a cross-sectional view of a representative composite of the present invention in a wetted state.
Figure 2C:
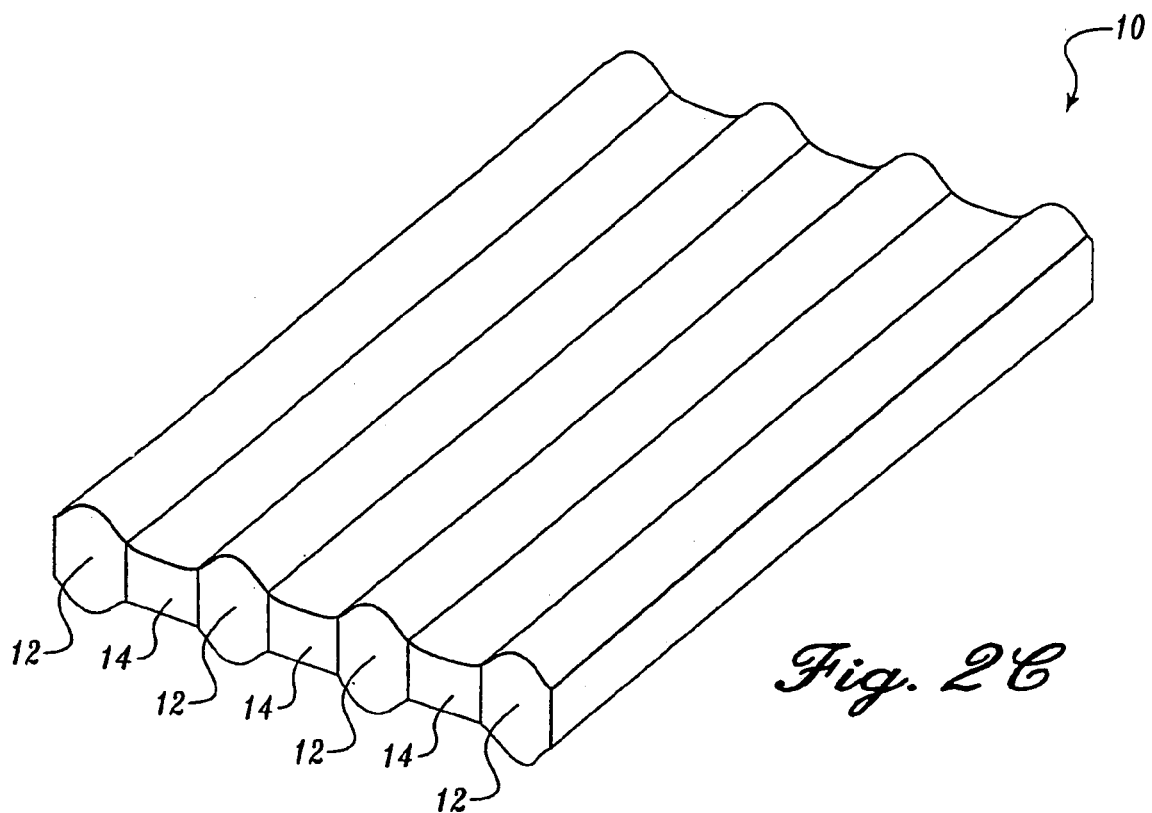
FIG. 2C is a perspective view of the wetted composite shown in FIG. 2B.
Figure 3:
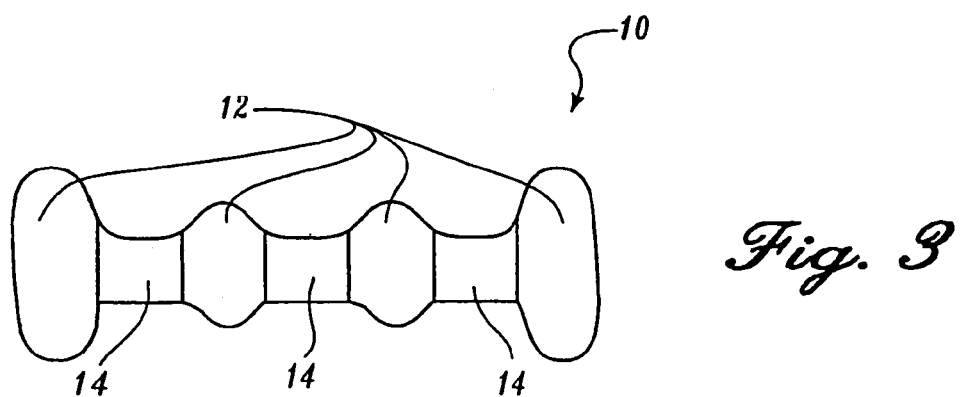
FIG. 3 is a cross-sectional view of a representative composite formed in accordance with the present invention.

The banded nature of the fluted absorbent composite is illustrated in FIGS. 1-3. Referring to FIG. 1, a representative fluted absorbent composite indicated generally by reference 10 formed in accordance with the present invention includes regions 12 enriched with absorbent material (i.e., liquid storage zones) and fibrous regions 14 that are substantially free of absorbent material (i.e., liquid distribution zones). Regions 12 enriched with absorbent material are generally fibrous regions to which have been added absorbent material.

When the absorbent composite is contacted with liquid, liquid is rapidly acquired by the predominantly fibrous regions of the composite. The fibrous regions are relatively open and porous in nature and promote rapid liquid acquisition, wicking, and distribution. Liquid acquired by the composite generally travels rapidly longitudinally through the fibrous composite along the composite's length via the distribution zones (i.e., regions 14) and is absorbed by regions of the composite enriched with absorbent material (i.e., regions 12). The acquired liquid is generally wicked laterally into the absorbent material as the liquid is distributed along the composite's length.

For the fluted composite, successive liquid insults are absorbed at a rate greater than the rate for initial insult through the establishment of flutes and channels on initial liquid insult. On wetting, the composite of the present invention becomes on a fluted structure having channels for rapidly acquiring additional liquid and distributing the liquid to sites that are remote to insult. Uptake of liquid by superabsorbent leads to expansion and enhancement of voids in the fibrous structure. For the fluted composite, acquisition times for subsequent liquid insult are generally less than that for the initial acquisition. Reduced acquisition times for successive liquid insults is not generally observed for conventional absorbent constructs. Because conventional absorbent structures cannot form a fluted structure and therefore lack channels for distributing additional liquid, acquisition times for these structures generally increase for successive liquid insults. Increased acquisition time is attributable to the fact that liquid is only slowly acquired and distributed through a composite's saturated regions to more remote regions of the composite that are capable of absorbing liquid. Thus, the fluted absorbent composite provides for initial liquid acquisition rates that are generally comparable or greater than for conventional absorbent structures and have significantly increased rates of liquid acquisition for successive liquid acquisition relative to conventional composites.

The dry and wet structures of the fluted composite are illustrated in FIGS. 2A and 2B, which are lateral cross-sectional views of a representative fluted absorbent composite. FIG. 2A is a cross-sectional view of the dry composite shown in FIG. 1 indicating regions 12 and 14 and the relatively uniform thickness of the unwetted composite. FIG. 2B is a cross-sectional view of the composite shown in FIG. 1 in a wetted state, for example, after liquid insult and liquid absorption and swelling and expansion of the absorbent material. Referring to FIG. 2B, absorbent material enriched regions 12 (i.e., liquid storage regions) are shown as ridges or flutes separated by fibrous regions 14 (i.e., liquid distribution zones) that form a valley floor or channel between the flutes. Due at least in part to the fluted structure of the wetted fibrous composite, subsequent liquid insults are rapidly absorbed by the fluted composite compared to composites containing absorbent material in other configurations, for example, composites in which the absorbent material is distributed substantially uniformly throughout the composite and that are particularly susceptible to gel blocking, low acquisition rates, and liquid leakage.

Liquid acquisition rates and times for a representative fluted absorbent composite are compared to those of storage cores having relatively uniform distributions of absorbent material in Example 1. Acquisition rates for the fluted absorbent composite were significantly greater than for commercially available cores which showed acquisition rates that decreased substantially with successive insults. In contrast, the composite of the invention maintained high rates for three insults. The fluted composite also exhibited rates greater than for a similarly composed wet composite having a relatively uniform distribution of absorbent material throughout the composite.

Example 2 compares the wicking characteristics of a representative fluted absorbent composite to a commercially available diaper core and a wet-laid fibrous core that contains superabsorbent material distributed substantially uniformly throughout the composite. The horizontal and vertical wicking results indicate that the air-laid commercial core has the poorest wicking characteristics, while the fluted composite having bands of absorbent material exhibits significantly enhanced wicking compared to a similarly composed composite that includes relatively uniformly distributed absorbent material.

Distribution of liquid from the site of insult throughout the composite demonstrates the composite's wicking capacity and efficiency of material utilization. The liquid distribution of a representative fluted composite is compared to two commercially available diaper cores in Example 3. The results indicate that, in contrast to the commercial cores which suffer from liquid accumulation at the site of insult, the fluted composite has nearly ideal distribution, distributing liquid throughout the entire composite and fully utilizing the composite's materials.

Because liquid insults are absorbed in a conventional storage core at a rate less than the average infant's urination rate, liquid can leak from the diaper at its edges. To prevent such leakage, diaper manufacturers have developed elaborate and expensive leg cuff gasketing systems that fit tightly about an infant's leg and is generally uncomfortable and leaves marks. When incorporated into a diaper as a storage core, the fluted composite of this invention overcome the problems of edge leaking associated with conventional storage cores. Accordingly, in one preferred embodiment, the fluted absorbent composite includes outermost bands of absorbent material that include relatively greater amounts of absorbent than the inner bands. Referring to FIG. 3, outermost absorbent material enriched regions 12 have a greater amount of absorbent material relative to the inner regions 12 and, as a consequence, have a greater absorbent capacity and therefore can swell and expand to greater size that those flutes containing relatively lesser amount of absorbent material. The fluted absorbent core having relatively greater amount of absorbent material in the outermost regions 12 can assist in the prevention of liquid leaking from the edge of the composite. In another preferred embodiment, outermost absorbent materials enriched regions 12 contain absorbent material having a higher absorptive and/or liquid retention capacity than the absorbent material contained in inner regions 12.

An infant's skin is always susceptible to irritation and rash resulting from moisture associated with retained liquid from a diaper's storage core. The amount of liquid released from an absorbent article that has acquired liquid is referred to as "rewet". While a storage core's surface is generally necessarily hydrophilic to effectively absorb liquid, such hydrophilic surfaces also promote rewet. In contrast to conventional absorbent articles that are in continuous contact with a wearer's skin, the fluted composite's surface contacts the wearer only at the flute's ridgetops thereby minimizing contact with the wearer's skin and rewet. Because of the minimized contact between an infant's skin and the wetted surface of the fluted absorbent composite compared to the wetted surface of a conventional storage core, the fluted absorbent composite offers advantages relating to skin health and comfort to the wearer. It is contemplated that the composite's fluted structure also provides skin health advantages related to cooling and air flow through an absorbent article that contains the fluted composite. The rewet performance of a representative fluted absorbent composite is compared to a commercially available diaper core in Example 1. Generally, for successive insults, rewet increases for the commercial core. In contrast, rewet remains low and substantially unchanged for the fluted composite.

The structure of fluted composite offers the possibility of further, reduction in rewet. Liquid insult generally occurs across the width of the composite which includes bands of fibrous regions and regions enriched with absorbent material. Liquid is generally rapidly acquired and distributed through the composite's fibrous regions (i.e., regions 14) and generally stored in the composite's regions enriched with absorbent material (i.e., regions 12). Ultimately, the acquired liquid resides in the bands of absorbent material in the fluted structure. To further reduce rewet, the fluted absorbent composite can include a hydrophobic barrier coincident with the top surface of the composite's flutes (i.e., coatings for the surfaces of regions 12). Suitable hydrophobic barriers generally include latex and other hydrophobic films and coatings known in the art. Because the distribution zones between the coated flutes (i.e., regions 14) are physically removed from the wearer and because the wearer is protected from the flutes containing the absorbent material and acquired liquid by a hydrophobic barrier, such a coated fluted composite provides for increased skin health through a reduction of skin wetness. Optionally, a hydrophobic barrier can also be affixed to the outward facing surface of the absorbent composite. Such a construction allows for a reduction in the thickness of the polyethylene moisture barrier (i.e., liquid impervious backing sheet) traditionally employed in a diaper. The application of a hydrophobic barrier to the outward surface of the composite would reduce total cost and material usage in an absorbent article incorporating the fluted absorbent composite.

Figure 4A:
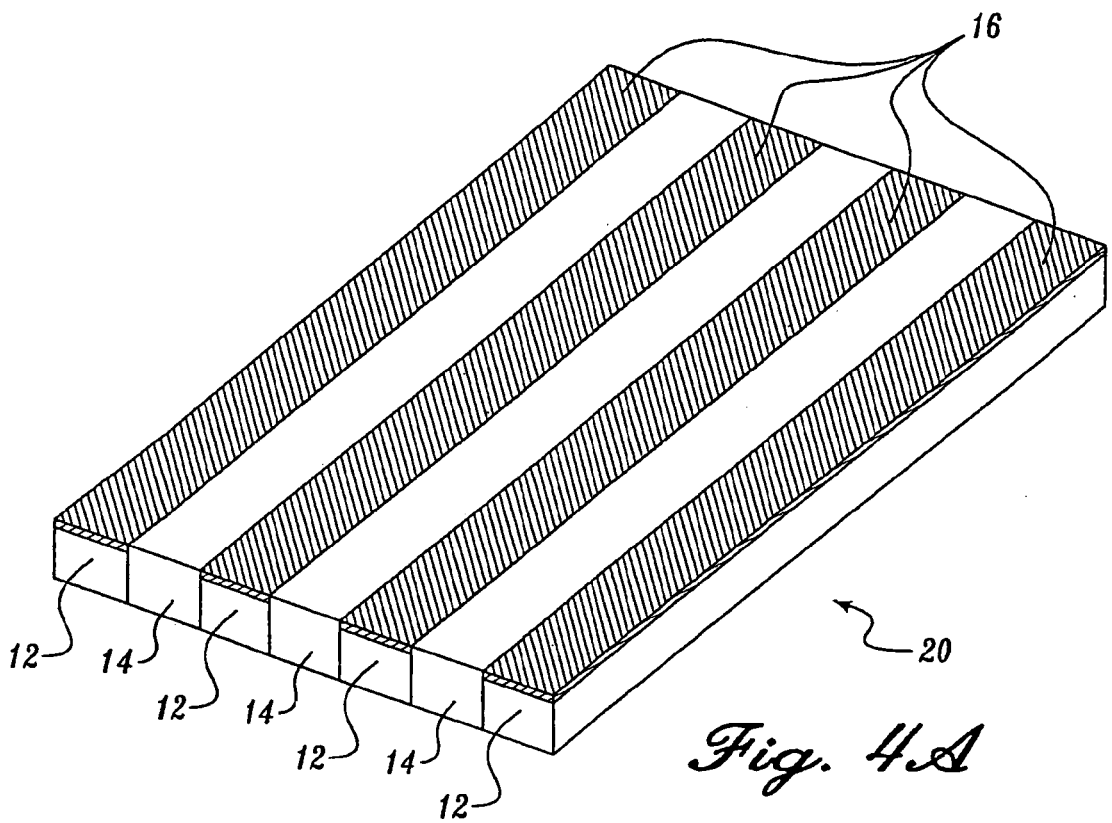
FIG. 4A is a perspective view of the upper surface of a representative composite formed in accordance with the present invention.
Figure 4B:
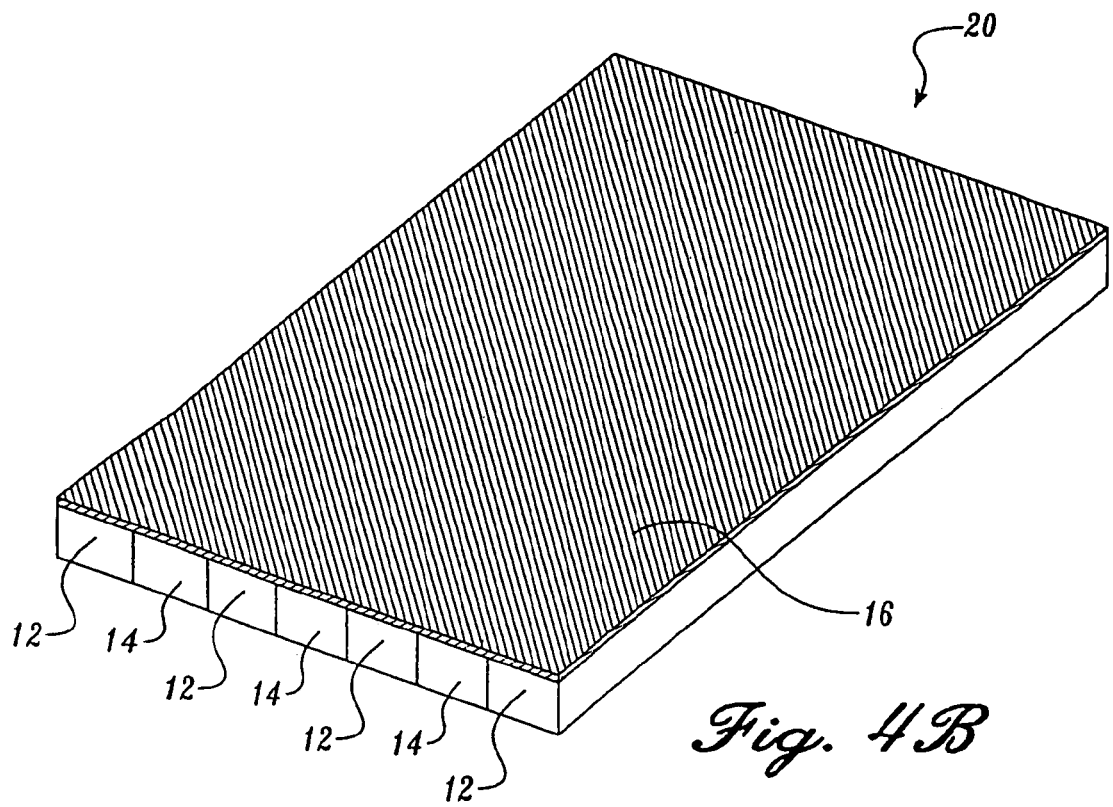
FIG. 4B is a perspective view of the lower surface of a representative composite formed in accordance with the present invention.

A representative fluted absorbent composite having a hydrophobic barrier coincident with the composite's bands of absorbent material and affixed to inward surface of the composite is illustrated in FIG. 4A. Referring to FIG. 4A, coated composite 20 includes regions 12 and 14, as described above, and hydrophobic barriers 16 substantially coincident with and covering regions 12 enriched with absorbent material. A representative fluted absorbent composite having a hydrophobic barrier affixed to the outward facing surface of a fluted absorbent composite is illustrated in FIG. 4B.

Fibers are a principal component of the fluted absorbent composite. Fibers suitable for use in the present invention are known to those skilled in the art and include any fiber from which an absorbent composite can be formed. Suitable fibers include natural and synthetic fibers. Combinations of fibers including combinations of synthetic and natural fibers, and treated and untreated fibers, can also be suitably used in the composite.

Generally, fibers are present in the composite in an amount from about 20 to about 90 weight percent, preferably from about 50 to about 70 weight percent, based on the total weight of the composite. In a preferred embodiment, the composite includes about 60 percent by weight fibers.

The composite includes resilient fibers. As used herein, the term "resilient fiber" refers to a fiber present in the composite that imparts reticulation to the composite. Generally, resilient fibers provide the composite with bulk and resiliency. The incorporation of resilient fibers into the composite allows the composite to expand on absorption of liquid without structural integrity loss. Resilient fibers also impart softness to the composite. In addition, resilient fibers offer advantages in the composite's formation processes. Because of the porous and open structure resulting from wet composites that include resilient fibers, these composites drain water relatively easily and are therefore dewatered and dried more readily than wet composites that do not include resilient fibers. Preferably, the composite includes resilient fibers in an amount from about 10 to about 60 percent by weight, more preferably from about 20 to 50 percent by weight, based on the total weight of the composite.

Resilient fibers include cellulosic and synthetic fibers. Preferred resilient fibers include chemically stiffened fibers, anfractuous fibers, chemithermomechanical pulp (CTMP), and prehydrolyzed kraft pulp (PHKP).

The term "chemically stiffened fiber" refers to a fiber that has been stiffened by chemical means to increase fiber stiffness under dry and wet conditions. Fibers can be stiffened by the addition of chemical stiffening agents that can coat and/or impregnate the fibers. Stiffening agents include the polymeric wet strength agents including resinous agents such as, for example, polyamide-epichlorohydrin and polyacrylamide resins described below. Fibers can also be stiffened by modifying fiber structure by, for example, chemical crosslinking. Preferably, the chemically stiffened fibers are intrafiber crosslinked cellulosic fibers.

Resilient fibers can include noncellulosic fibers including, for example, synthetic fibers such as polyolefin, polyamide, and polyester fibers. In a preferred embodiment, the resilient fibers include crosslinked cellulosic fibers.

As used herein, the term "anfractuous fiber" refers to a cellulosic fiber that has been chemically treated. Anfractuous fibers include, for example, fibers that have been treated with ammonia.

In addition to resilient fibers, the composite includes matrix fibers. As used herein, the term "matrix fiber" refers to a fiber that is capable of forming hydrogen bonds with other fibers. Matrix fibers are included in the composite to impart strength to the composite. Matrix fibers include cellulosic fibers such as wood pulp fibers, highly refined cellulosic fibers, and high surface area fibers such as expanded cellulose fibers. Other suitable cellulosic fibers include cotton linters, cotton fibers, and hemp fibers, among others. Preferably, the composite includes matrix fibers in an amount from about 10 to about 50 percent by weight, more preferably from about 15 to about 30 percent by weight, based on the total weight of the composite.

The composite preferably includes a combination of resilient and matrix fibers. In one preferred embodiment, the composite includes resilient fibers in an amount from about 25 to about 50 percent by weight and matrix fibers in an amount from about 10 to about 40 percent by weight based on the total weight of the composite. In a more preferred embodiment, the composite includes from about 30 to about 45 percent by weight resilient fibers, preferably crosslinked cellulosic fibers, and from about 15 to about 30 percent by weight matrix fibers, preferably wood pulp fibers, based on the total weight of fibers in the composite. For representative composites formed by wet-laid and foam processes, the composite preferably includes about 45 percent by weight resilient fibers (e.g., crosslinked cellulosic fibers) and about 15 percent by weight matrix fibers.

Cellulosic fibers can be a basic component of the fluted absorbent composite. Although available from other sources, cellulosic fibers are derived primarily from wood pulp. Suitable wood pulp fibers for use in the invention can be obtained from well-known chemical processes such as the kraft and sulfite processes, with or without subsequent bleaching. Pulp fibers can also be processed by thermomechanical, chemithermomechanical methods, or combinations thereof. The preferred pulp fiber is produced by chemical methods. Ground wood fibers, recycled or secondary wood pulp fibers, and bleached and unbleached wood pulp fibers can be used. Softwoods and hardwoods can be used. Details of the selection of wood pulp fibers are well-known to those skilled in the art. These fibers are commercially available from a number of companies, including Weyerhaeuser Company, the assignee of the present invention. For example, suitable cellulose fibers produced from southern pine that are usable in the present invention are available from Weyerhaeuser Company under the designations CF416, NF405, PLM16, FR516, and NB416.

The wood pulp fibers can also be pretreated prior to use in the present invention. This pretreatment may include physical treatment, such as subjecting the fibers to steam, or chemical treatment, for example, crosslinking the cellulose fibers using any one of a variety of crosslinking agents. Crosslinking increases fiber bulk and resiliency, and thereby can improve the fibers' absorbency. Generally, crosslinked fibers are twisted or crimped. The use of crosslinked fibers allows the composite to be more resilient, softer, bulkier, and to have enhanced wicking. Suitable crosslinked cellulose fibers produced from southern pine are available from Weyerhaeuser Company under the designation NBH416. Crosslinked cellulose fibers and methods for their preparation are disclosed in U.S. Pat. Nos. 5,437,418 and 5,225,047 issued to Graef et al., expressly incorporated herein by reference.

Crosslinked fibers can be prepared by treating fibers with a crosslinking agent. Suitable cellulose crosslinking agents include aldehyde and urea-based formaldehyde addition products. See, for example, U.S. Pat. Nos. 3,224,926; 3,241,533; 3,932,209; 4,035,147; 3,756,913; 4,689,118; 4,822,453; U.S. Pat. No. 3,440,135, issued to Chung; U.S. Pat. No. 4,935,022, issued to Lash et al.; U.S. Pat. No. 4,889,595, issued to Herron et al.; U.S. Pat. No. 3,819,470, issued to Shaw et al.; U.S. Pat. No. 3,658,613, issued to Steiger et al.; and U.S. Pat. No. 4,853,086, issued to Graef et al., all of which are expressly incorporated herein by reference in their entirety. Cellulose fibers have also been crosslinked by carboxylic acid crosslinking agents including polycarboxylic acids. U.S. Pat. Nos. 5,137,537; 5,183,707; and 5,190,563, describe the use of $C_2$–$C_9$ polycarboxylic acids that contain at least three carboxyl groups (e.g., citric acid and oxydisuccinic acid) as crosslinking agents.

Suitable urea-based crosslinking agents include methylolated ureas, methylolated cyclic ureas, methylolated lower alkyl substituted cyclic ureas, methylolated dihydroxy cyclic ureas, dihydroxy cyclic ureas, and lower alkyl substituted cyclic ureas. Specific preferred urea-based crosslinking agents include dimethylol urea (DMU, bis[N-hydroxymethyl]urea), dimethylolethylene urea (DMEU, 1,3-dihydroxymethyl-2-imidazolidinone), dimethyloldihydroxyethylene urea (DMDHEU, 1,3-dihydroxymethyl-4,5-dihydroxy-2-imidazolidinone), dimethyldihydroxy urea (DMDHU), dihydroxyethylene urea (DHEU, 4,5-dihydroxy-2-imidazolidinone), and dimethyldihydroxyethylene urea (DMeDHEU, 4,5-dihydroxy-1,3-dimethyl-2-imidazolidinone).

Suitable polycarboxylic acid crosslinking agents include citric acid, tartaric acid, malic acid, succinic acid, glutaric acid, citraconic acid, itaconic acid, tartrate monosuccinic acid, and maleic acid. Other polycarboxylic acids crosslinking agents include polymeric polycarboxylic acids such as poly(acrylic acid), poly(methacrylic acid), poly(maleic acid), poly(methylvinylether-co-maleate) copolymer, poly(methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. patent application Ser. No. 08/989,697, filed Dec. 12, 1997, and assigned to Weyerhaeuser Company. Mixtures or blends of crosslinking agents may also be used.

The crosslinking agent can include a catalyst to accelerate the bonding reaction between the crosslinking agent and cellulose fiber. Suitable catalysts include acidic salts, such as ammonium chloride, ammonium sulfate, aluminum chloride, magnesium chloride, and alkali metal salts of phosphorous-containing acids.

Although not to be construed as a limitation, examples of pretreating fibers include the application of surfactants or other liquids which modify the surface chemistry of the fibers. Other pretreatments include incorporation of antimicrobials, pigments, dyes and densification or softening agents. Fibers pretreated with other chemicals, such as thermoplastic and thermosetting resins also may be used. Combinations of pretreatments also may be employed. Similar treatments can also be applied after the composite formation in post-treatment processes.

Cellulosic fibers treated with particle binders and/or densification/softness aids known in the art can also be employed in accordance with the present invention. The particle binders serve to attach other materials, such as cellulosic fiber superabsorbent polymers, as well as others, to the cellulosic fibers. Cellulosic fibers treated with suitable particle binders and/or densification/softness aids and the process for combining them with cellulose fibers are disclosed in the following U.S. patents: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Binders"; (4) U.S. Pat. No. 5,352,480, entitled "Method for Binding Particles to Fibers Using Reactivatable Binders"; (5) U.S. Pat. No. 5,308,896, entitled "Particle Binders for High-Bulk Fibers"; (6) U.S. Pat. No. 5,589,256, entitled "Particle Binders that Enhance Fiber Densification"; (7) U.S. Pat. No. 5,672,418, entitled "Particle Binders"; (8) U.S. Pat. No. 5,607,759, entitled "Particle Binding to Fibers"; (9) U.S. Pat. No. 5,693,411, entitled "Binders for Binding Water Soluble Particles to Fibers"; (10) U.S. Pat. No. 5,547,745, entitled "Particle Binders"; (11) U.S. Pat. No. 5,641,561, entitled "Particle Binding to Fibers"; (12) U.S. Pat. No. 5,308,896, entitled "Particle Binders for High-Bulk Fibers"; (13) U.S. Pat. No. 5,498,478, entitled "Polyethylene Glycol as a Binder Material for Fibers"; (14) U.S. Pat. No. 5,609,727, entitled "Fibrous Product for Binding Particles"; (15) U.S. Pat. No. 5,571,618, entitled "Reactivatable Binders for Binding Particles to Fibers"; (16) U.S. Pat. No. 5,447,977, entitled "Particle Binders for High Bulk Fibers"; (17) U.S. Pat. No. 5,614,570, entitled "Absorbent Articles Containing Binder Carrying High Bulk Fibers; (18) U.S. Pat. No. 5,789,326, entitled "Binder Treated Fibers"; and (19) U.S. Pat. No. 5,611,885, entitled "Particle Binders"; all expressly incorporated herein by reference.

In addition to natural fibers, synthetic fibers including polymeric fibers, such as polyolefin, polyamide, polyester, polyvinyl alcohol, polyvinyl acetate fibers, and can also be used in the absorbent composite. Suitable synthetic fibers include, for example, polyethylene terephthalate, polyethylene, polypropylene, nylon, and rayon fibers. Other suitable synthetic fibers include those made from thermoplastic polymers, cellulosic and other fibers coated with thermoplastic polymers, and multicomponent fibers in which at least one of the components includes a thermoplastic polymer. Single and multicomponent fibers can be manufactured from polyester, polyethylene, polypropylene, and other conventional thermoplastic fibrous materials. Single and multicomponent fibers are commercially available. Suitable bicomponent fibers include Celbond® fibers available from Hoechst-Celanese Company. The absorbent composite can also include combinations of natural and synthetic fibers. Synthetic fibers, including blends of natural and synthetic fibers, can be utilized in the composite's flutes and/or distribution zones.

In one preferred embodiment, the absorbent composite includes a combination of pulp fibers (e.g., Weyerhaeuser designation NB416) and crosslinked cellulosic fibers (e.g., Weyerhaeuser designation NHB416). In a preferred embodiment, the absorbent composite includes a combination of pulp fibers present in the composite in about 50 weight percent and crosslinked cellulosic fibers present in the composite in about 50 weight percent based on the total weight of fibers.

In a preferred embodiment, the wet-laid or foam-formed fluted composite is formed from a fiber furnish that includes a blend of refined southern pine fibers and crosslinked fibers. Composites formed from such a blend have increased sheet integrity and enhanced bulk compared to composites formed from a mixture of southern pine and crosslinked fibers that has been refined. Optionally, the blend of refined southern pine fibers and crosslinked fibers can be further lightly refined.

The fluted absorbent composite can serve as a storage layer for acquired liquids when incorporated into an absorbent article. To effectively retain acquired liquids, the composite includes absorbent material.

Figure 5:
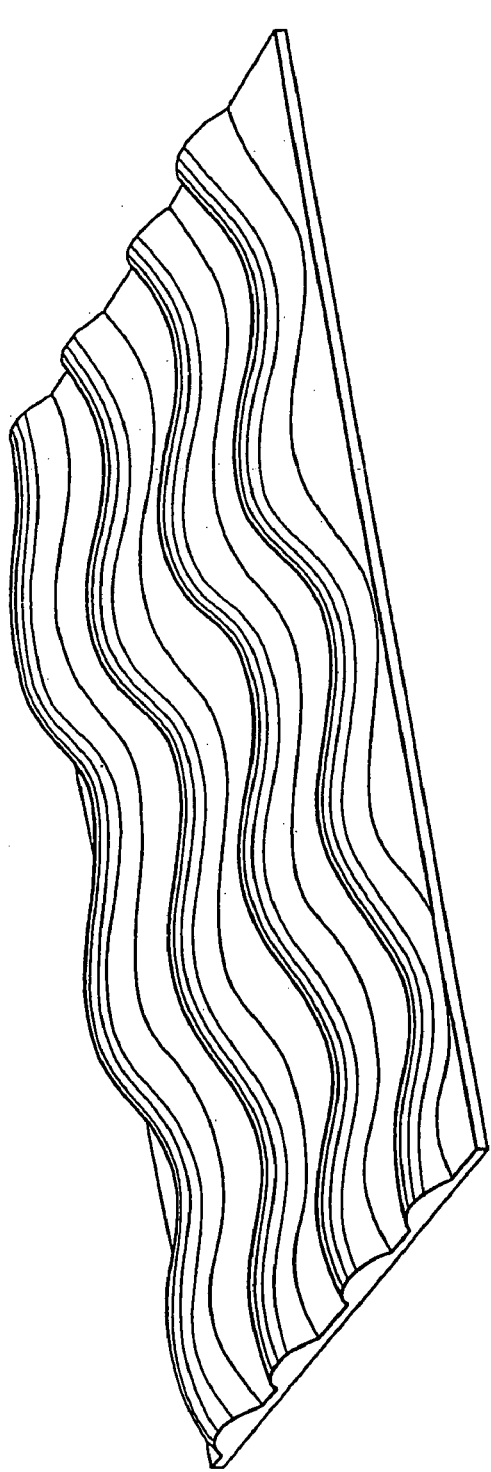
FIG. 5 is a perspective view of a representative absorbent material banding pattern formed in accordance with the present invention.
Figure 6:
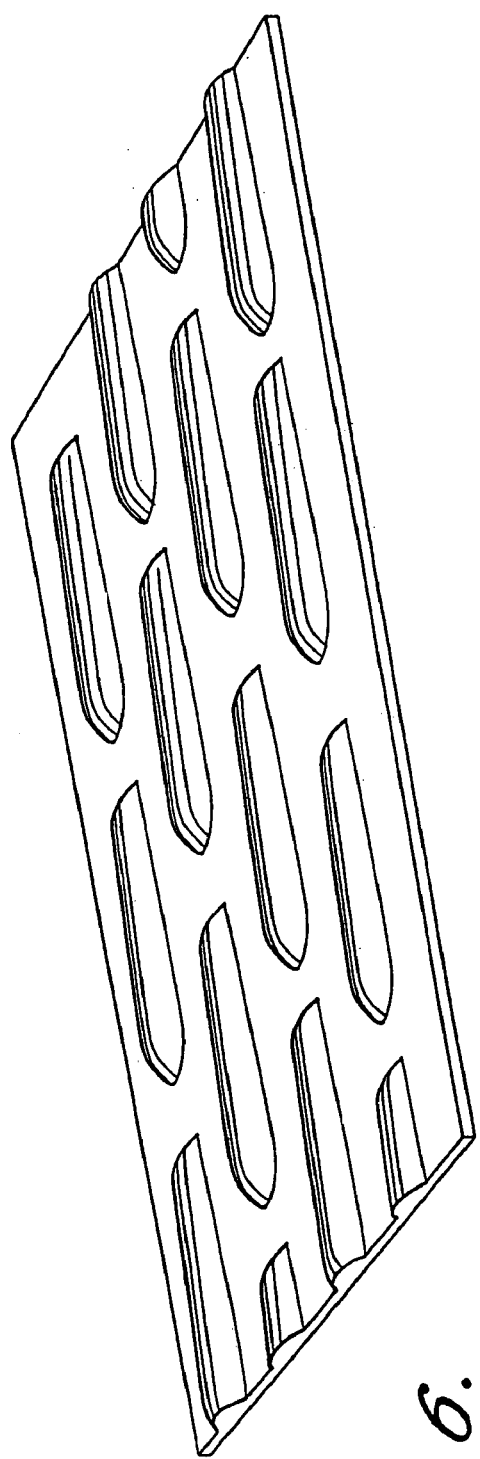
FIG. 6 is a perspective view of another representative absorbent material banding pattern formed in accordance with the present invention.
Figure 7:
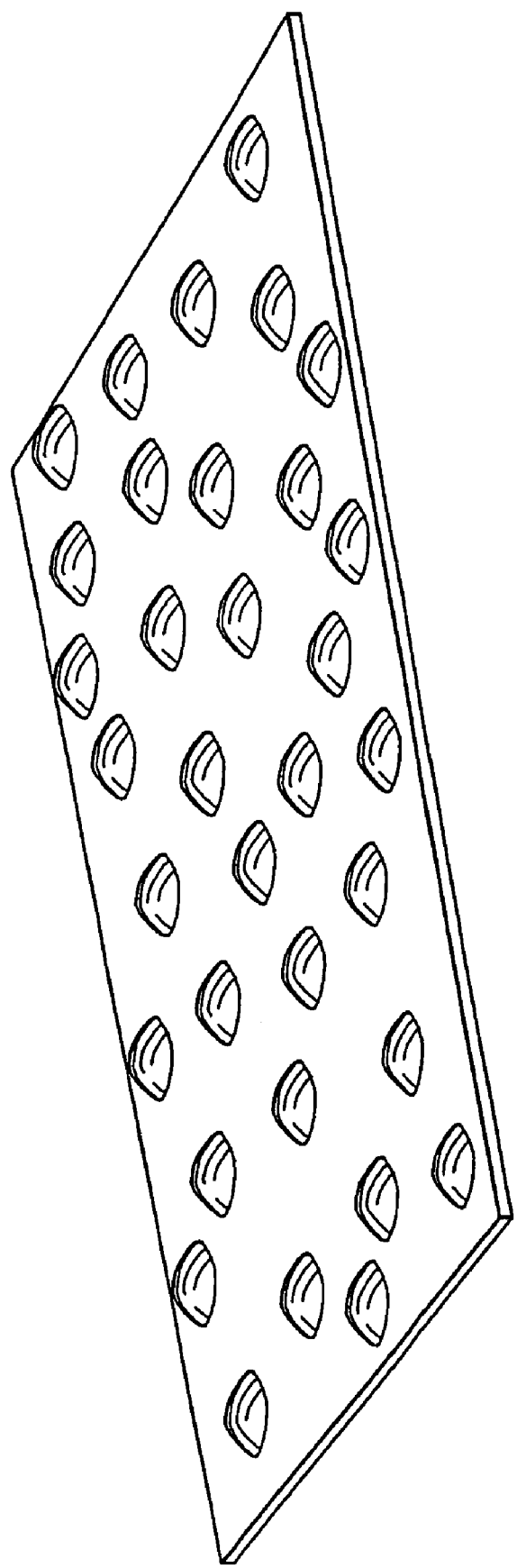
FIG. 7 is a perspective view of another representative absorbent material banding pattern formed in accordance with the present invention.

As described above, absorbent material is located in bands incorporated into the fibrous composite. Basically, bands of absorbent material can be configured in virtually any shape, size, and composite location. Suitable configurations of the composite's bands include any configuration that does not impede liquid acquisition or promote gel blocking. The bands of absorbent material can include straight and parallel bands, curved or wavy bands, and zigzag bands, among others. A representative banded absorbent composite having wavy bands is illustrated in FIG. 5. The composite's bands can also include pulsed bands of absorbent material. As used herein the term "pulsed band" refers to a band that extends along the composite's length that is not a continuous band, but rather is a band that is interrupted by regions containing substantially no absorbent material. A function of the pulsed bands is to provide the composite with enhanced liquid distribution capacity across the composite's width (i.e., the cross-machine direction). A representative banded absorbent composite having pulsed bands is illustrated in FIG. 6. As illustrated in FIG. 6, in one embodiment, the pulsed bands have an offset configuration to further enhance cross-machine direction liquid distribution. Such an offset configuration of absorbent material can be formed by injecting absorbent material into the composite through nozzles delivering nonsynchronous pulses of absorbent material (i.e., pulses from one nozzle that is not synchronized with pulses from another nozzle). The length of the pulsed band can vary greatly and can, for example, be a dot or spot of absorbent material having a length equal to about its width. A representative banded absorbent composite having pulsed bands resembling dots or spots is illustrated in FIG. 7.

The composite's bands or flutes are regions of the composite that are enriched with absorbent material. The composite's distribution zones can include some absorbent material. It will be appreciated that while absorbent material is incorporated into the composite in bands, the formation of absorbent material bands in the composite can lead to the introduction of some absorbent material into the composite's fibrous distribution zones. The incorporation of absorbent material into the composite can result in some mixing between the absorbent material and fibers present in the fibrous base. The result is a transition zone between the primarily fibrous distribution zones and the absorbent material bands. Such a transition zone includes both fibers and absorbent material. The composite's fibrous matrix can also be formed to include some absorbent materials thereby resulting in distribution zones containing absorbent material. In embodiments having absorbent material in the distribution zones, the amount of absorbent material present is not so great as to diminish the effectiveness of these zones in distributing acquired liquid.

Figure 8:
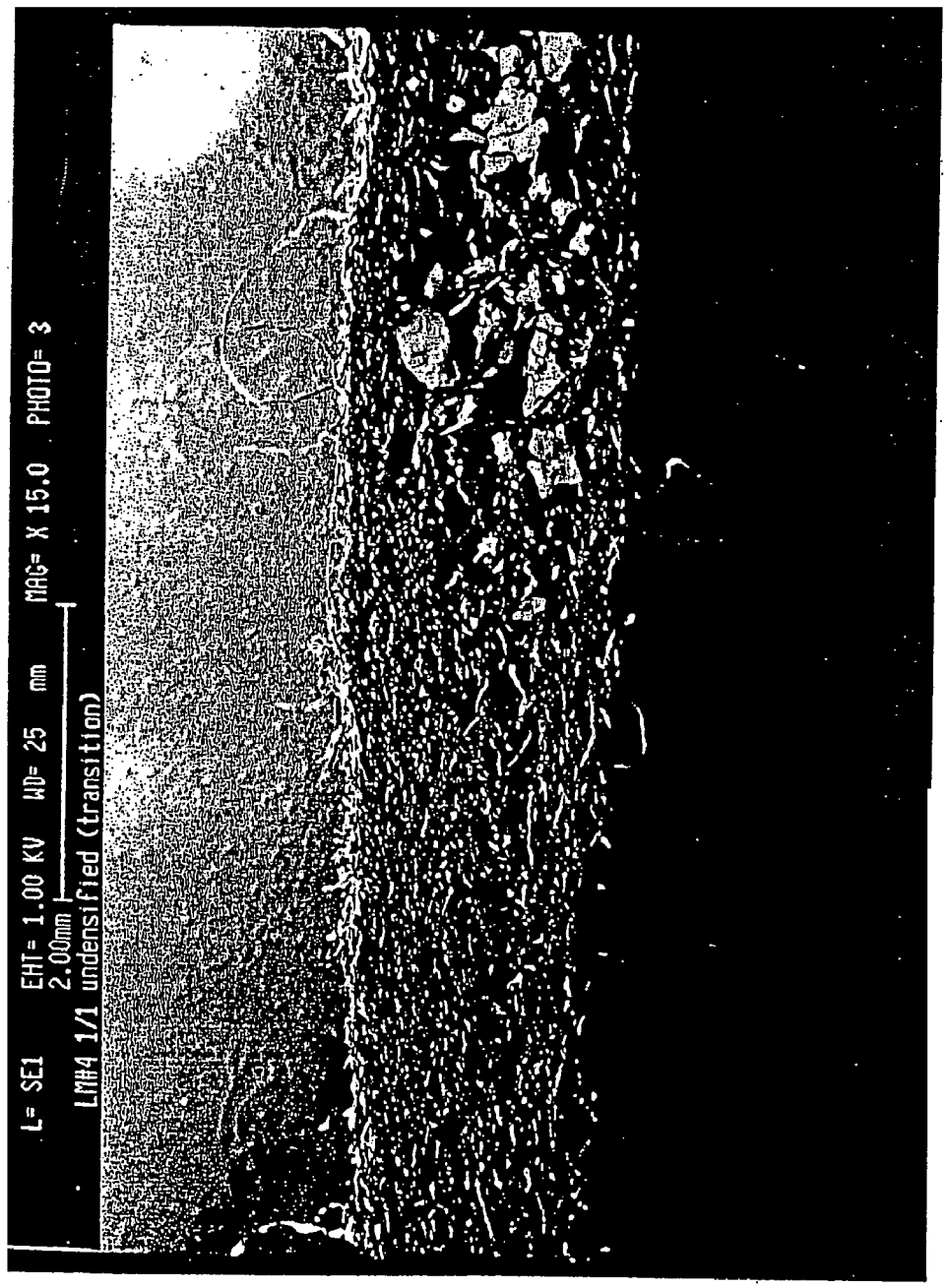
FIG. 8 is a photomicrograph (15× magnification) of a portion of a representative composite formed in accordance with the present invention, the photomicrograph shows a machine direction view of a cross-machine direction cut through a region enriched with absorbent material.
Figure 9:
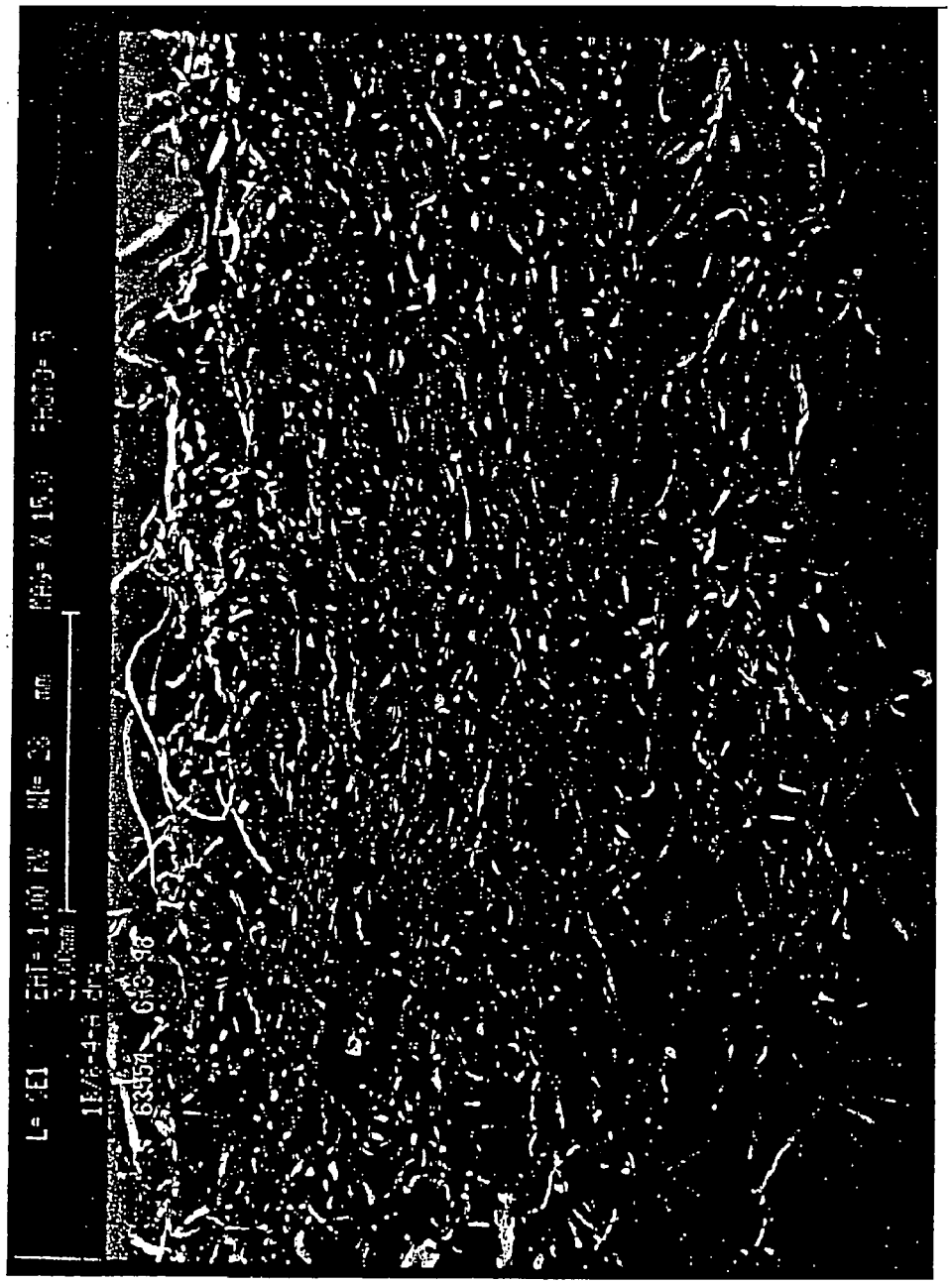
FIG. 9 is a photomicrograph (15× magnification) of a portion of a representative composite formed in accordance with the present invention, the photomicrograph shows a machine direction view of a cross-machine direction cut through a liquid distribution zone.
Figure 10:
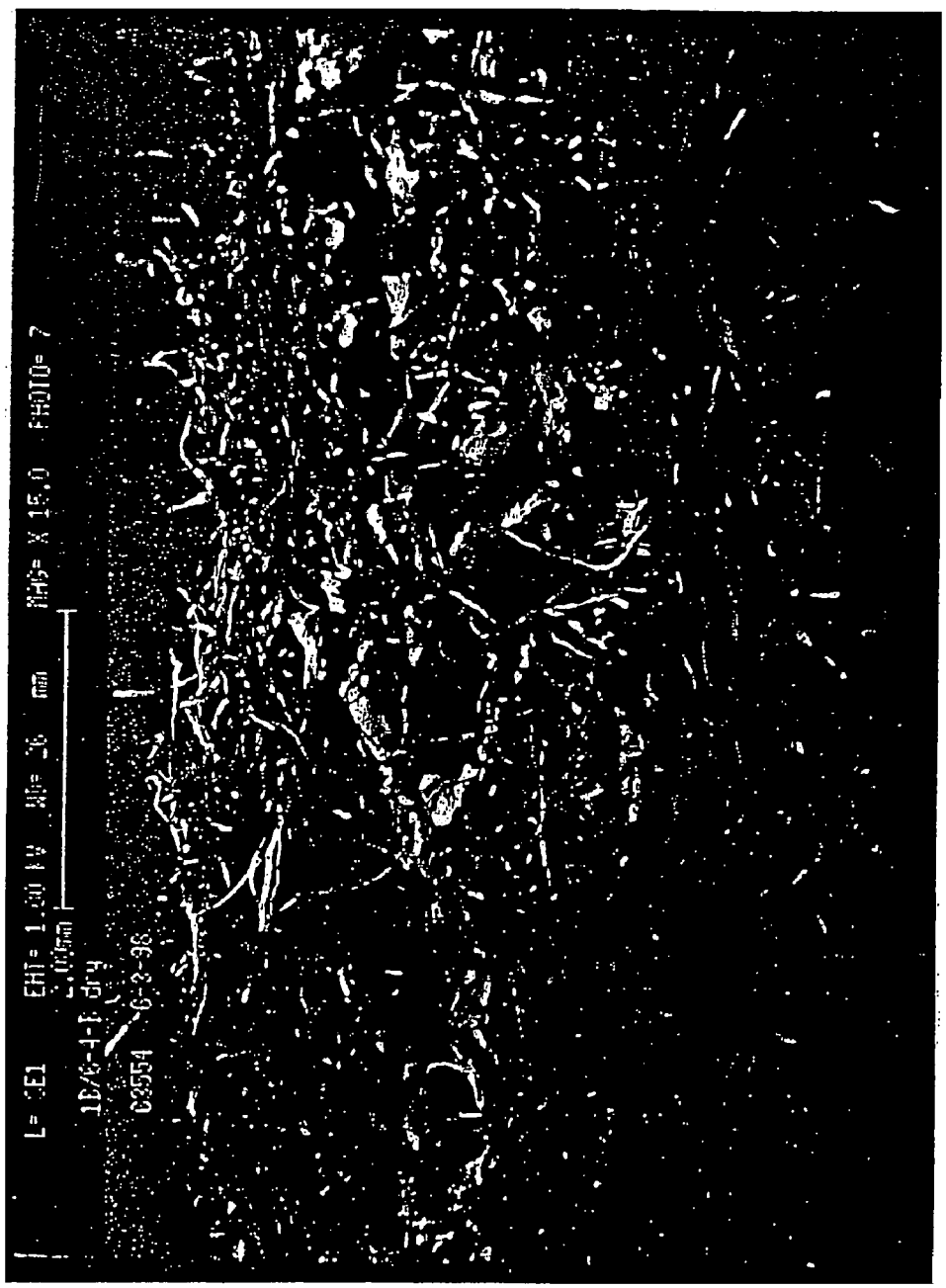
FIG. 10 is a photomicrograph (15× magnification) of a portion of a representative composite formed in accordance with the present invention, the photomicrograph shows a machine direction view of a cross-machine direction cut through an interface region of the composite between a liquid distribution zone and a region enriched with absorbent material.

Cross-sectional views of a representative composite formed by a wet-laid method are shown in the photomicrographs in FIGS. 8–10. FIG. 8 is a machine direction view of a cross-machine direction cut through the composite's absorbent material band (i.e., region 12 of the composite enriched with absorbent material). FIG. 9 is a machine direction view of a cross-machine direction cut through a distribution zone (i.e., region 14 of the composite substantially free of absorbent material). FIG. 10 is a machine direction view of a cross-machine direction cut intermediate an absorbent material band and a distribution zone (i.e., through a transition zone as described above).

As use herein, the term "absorbent material" refers to a material that absorbs liquid and that generally has an absorbent capacity greater than the cellulosic fibrous component of the composite. Preferably, the absorbent material is a water swellable, generally water insoluble polymeric material capable of absorbing at least about 5, desirably about 20, and preferably about 100 times or more its weight in saline (e.g., 0.9 percent saline). The absorbent material can be swellable in the dispersion medium utilized in the method for forming the composite. In one embodiment, the absorbent material is untreated and swellable in the dispersion medium. In another embodiment, the absorbent material is an absorbent material that is resistant to absorbing water during the composite formation process. Such absorbent materials that are resistant to absorption include coated and chemically modified absorbent materials.

The amount of absorbent material present in the composite can vary greatly depending on the composite's intended use. When the absorbent composite is used as a stand alone absorbent composite as in, for example, an absorbent toweling, the amount of absorbent material in the composite is comparative low (e.g., about 0.1 weight percent). The amount of absorbent material present in an absorbent article such as an absorbent core for an infant's diaper is considerably greater. In such a construct, the absorbent material is suitably present in the composite in an amount from about 10 to about 80 weight percent, preferably from about 30 to about 50 weight percent, based on the total weight of the composite. In preferred embodiments, the composite includes about 40 percent by weight absorbent material based on the total weight of the composite.

The absorbent material may include natural materials such as agar, pectin, and guar gum, and synthetic materials, such as synthetic hydrogel polymers. Synthetic hydrogel polymers include, for example, carboxymethyl cellulose, alkaline metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulphonic acid, polyacrylates, polyacrylamides, and polyvinyl pyridine among others. In a preferred embodiment, the absorbent material is a superabsorbent material. As used herein, a "superabsorbent material" refers to a polymeric material that is capable of absorbing large quantities of fluid by swelling and forming a hydrated gel (i.e., a hydrogel). In addition to absorbing large quantities of fluids, superabsorbent polymers can also retain significant amounts of bodily fluids under moderate pressure.

Superabsorbent polymers generally fall into three classes: starch graft copolymers, crosslinked carboxymethylcellulose derivatives, and modified hydrophilic polyacrylates. Examples of such absorbent polymers include hydrolyzed starch-acrylonitrile graft copolymers, neutralized starch-acrylic acid graft copolymers, saponified acrylic acid ester-vinyl acetate copolymers, hydrolyzed acrylonitrile copolymers or acrylamide copolymers, modified crosslinked polyvinyl alcohol, neutralized self-crosslinking polyacrylic acids, crosslinked polyacrylate salts, carboxylated cellulose, and neutralized crosslinked isobutylene-maleic anhydride copolymers.

Superabsorbent polymers are available commercially, for example, polyacrylates from Clariant of Portsmouth, Va. These superabsorbent polymers come in a variety of sizes, morphologies and absorbent properties (available from Clariant under trade designations such as IM 3500 and IM 3900). Other superabsorbent particles are marketed under the trademarks SANWET (supplied by Sanyo Kasei Kogyo Kabushiki Kaisha), and SXM77 (supplied by Stockhausen of Greensboro, N.C.). Other superabsorbent polymers are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598, all expressly incorporated herein by reference. Products such as diapers that incorporate superabsorbent polymers are described in U.S. Pat. No. 3,699,103 and U.S. Pat. No. 3,670,731.

Suitable superabsorbent polymers useful in the absorbent composite include superabsorbent polymer particles and superabsorbent polymer fibers.

In a preferred embodiment, the absorbent composite includes a superabsorbent material that that swells relatively slowly for the purposes of composite manufacturing and yet swells at an acceptable rate so as not to adversely affect the absorbent characteristics of the composite or any construct containing the composite.

In one embodiment, the present invention provides a composite having absorbent material present in the composite in a concentration gradient. As used herein, the term "concentration gradient" refers to a gradient in the concentration of absorbent material in the fibrous composite with respect to a particular dimension (i.e., thickness, width, and length) of the composite. An absorbent material concentration gradient is formed through selective distribution of the material into the composite. For example, as described below, introduction of the absorbent material into the composite can be accomplished with significant fiber mixing and an accompanying loss of an absorbent material concentration gradient. Alternatively, the absorbent material can be introduced into the composite without significant fiber mixing resulting in the formation of a relatively greater concentration gradient. The composite's concentration gradient can be present in either the z-direction (i.e., the thickness of the composite), the x-direction (i.e., across the width of the composite, the cross-machine direction), the y-direction (i.e., along the length of the composite, the machine direction) or combinations of the x-, y- and z-directions. Concentration gradients of absorbent material are contemplated to increase liquid wicking and further to reduce the potential for gel blocking.

In another embodiment, the present invention provides a banded composite having absorbent material relatively uniformly distributed across its width and extending along its length throughout its thickness in addition to absorbent material present in the bands. The absorbent material is distributed into the fibrous composite as described below and preferably is present in the composite in a concentration gradient. Preferably the concentration gradient is present in at least the z-direction (i.e., the composite's thickness), although gradients in the x- and y-directions are also contemplated to provide useful composites. Composites include those having concentration gradients in one or more of the x-, y-, and z-directions. For embodiments having a z-direction gradient, the high concentration surface is preferably positioned in an absorbent article away from liquid insult. In one embodiment having a concentration gradient in the x-direction (i.e., the composite's width), the concentration is preferably maximal at center of the composite's width and decreases outwardly from the center toward the composite's edges. In another embodiment, the concentration is preferably maximal at the composite's edges. Gradients in the y-direction generally provide regions of absorbent material along the composite's length.

The absorbent composite optionally includes a wet strength agent. The wet strength agent provides increased strength to the absorbent composite and enhances the composites wet integrity. In addition to increasing the composites wet strength, the wet strength agent can assist in binding the absorbent material, for example, superabsorbent material, in the composite's fibrous matrix.

Suitable wet strength agents include cationic modified starch having nitrogen-containing groups (e.g., amino groups) such as those available from National Starch and Chemical Corp., Bridgewater, N.J.; latex; wet strength resins such as polyamide-epichlorohydrin resin (e.g., Kymene® 557LX, Hercules, Inc., Wilmington, Del.), polyacrylamide resin (described, for example, in U.S. Pat. No. 3,556,932 issued Jan. 19, 1971 to Coscia et al.; also, for example, the commercially available polyacrylamide marketed by American Cyanamid Co., Stanford, Conn., under the trade name Parez™ 631 NC); urea formaldehyde and melamine formaldehyde resins, and polyethylenimine resins. A general discussion on wet strength resins utilized in the paper field, and generally applicable in the present invention, can be found in TAPPI monograph series No. 29, "Wet Strength in Paper and Paperboard", Technical Association of the Pulp and Paper Industry (New York, 1965).

Generally, the wet strength agent is present in the composition in an amount from about 0.01 to about 2 weight percent, preferably from about 0.1 to about 1 weight percent, and more preferably from about 0.3 to about 0.7 weight percent, based on the total weight of the composite. In a preferred embodiment, the wet strength agent useful in the composite is a polyamide-epichlorohydrin resin such as commercially available from Hercules, Inc. under the designation Kymene®. The wet and dry tensile strength of an absorbent composite formed in accordance with the present invention will generally increase with an increasing the amount of wet strength agent.

It has been observed that after successive liquid insults, the composites formed in accordance with the present invention maintain their structural integrity and remain substantially intact on removal from a diaper construct. In contrast, conventional storage cores that contain superabsorbent material lose structural integrity in a wetted diaper. Thus, the wet tensile strength of the fluted absorbent cores significantly exceeds that of conventional storage cores.

The absorbent composite generally has a basis weight from about 50 to about 1000 g/m$^2$, and preferably from about 200 to about 800 g/m$^2$. In a more preferred embodiment, the absorbent composite has a basis weight from about 300 to about 600 g/m$^2$. The basis weight of the fluted composite can be varied and will depend on its intended use. When the fluted composite's intended use is as a storage layer, the composite preferably has a basis weight greater than about 300 g/m$^2$. For use as a liquid management layer, the composite preferably has a basis weight from about 100 to about 400 g/m$^2$. The absorbent composite generally has an average density (in the cross-machine direction) of from about 0.03 to about 0.8 g/cm$^3$, preferably from about 0.04 to about 0.3 g/cm$^3$. In a more preferred embodiment, the absorbent composite has an average density of about 0.15 g/cm$^3$.

In one embodiment, the absorbent composite is a densified composite. Densification methods useful in producing the densified composites are well known to those in the art. See, for example, U.S. Pat. No. 5,547,541 and patent application Ser. No. 08/859,743, filed May 21, 1997, entitled "Softened Fibers and Methods of Softening Fibers," assigned to Weyerhaeuser Company, both expressly incorporated herein by reference. Post dryer densified absorbent composites generally have a density from about 0.1 to about 0.5 g/cm$^3$, and preferably about 0.15 g/cm$^3$. Predryer densification can also be employed. Preferably, the absorbent composite is densified by either a heated or room temperature calender roll method. See, for example, U.S. Pat. Nos. 5,252,275 and 5,324,575, both expressly incorporated herein by reference.

The composition of the absorbent composite can be varied to suit the intended use of the end product in which the composite is incorporated. In one preferred embodiment, the absorbent composite includes about 60 weight percent cellulosic fibers, about 40 percent by weight absorbent material (e.g., superabsorbent polymeric particles), and about 0.25 percent by weight wet strength agent (e.g., polyamide-epichlorohydrin resin, Kymene®, about 2–20 pounds resin per ton fiber) based on the total weight of the composite.

The dimensions of the fluted absorbent composite can be varied greatly depending on the desired characteristics of the composite and its intended use. Typically, for a child's diaper, the composite includes from about 2 to about 6 bands of absorbent material across the composite's width, the outward edges of the composite preferably including bands of absorbent material. For a typical adult incontinence product, the composite can include 10 or more bands. Although the configuration and widths of the bands are not particularly critical, the bands of absorbent material are generally evenly spaced across the composite's width and have widths of from about 0.10 to about 0.75 inch. The bands are typically separated by distribution zones having widths from about 0.10 to about 1.0 inch. Feminine care products contain a relatively low amount of absorbent material and fluted composites useful in such products have relatively narrow bands of absorbent material.

The present invention provides methods for forming a fluted absorbent composite. The fluted structure of the composite can be formed in any one of variety of methods known to those in the art, all of which are within the scope of this invention. For example, a fluted structure can be formed by attaching one of more bands of absorbent material or acquisition/distribution material to a fibrous base; depositing, injecting, applying, impregnating, or infusing absorbent material into a fibrous base; or by wet-laid and foam-forming processes as described below.

For embodiments that are formed by attaching bands of absorbent or acquisition/distribution materials to a fibrous base, the bands can further include other materials such as fibers. For these embodiments, the absorbent material-containing bands and the fibrous base can be independently formed by methods known to those in the art including air-laid, wet-laid, and foam-forming methods, as described below. The fluted composite can be formed by affixing or attaching the bands to a fibrous base by any method that permits fluid communication between these components of the composite. Suitable means for affixing or attaching include, for example, gluing, thermobonding, and entangling. Generally, these embodiments have improved absorbent properties due to enhanced fluid communication between the composite's components compared to the composites that have absorbent material in mere proximity to the composite's fibrous component.

Figure 11A:
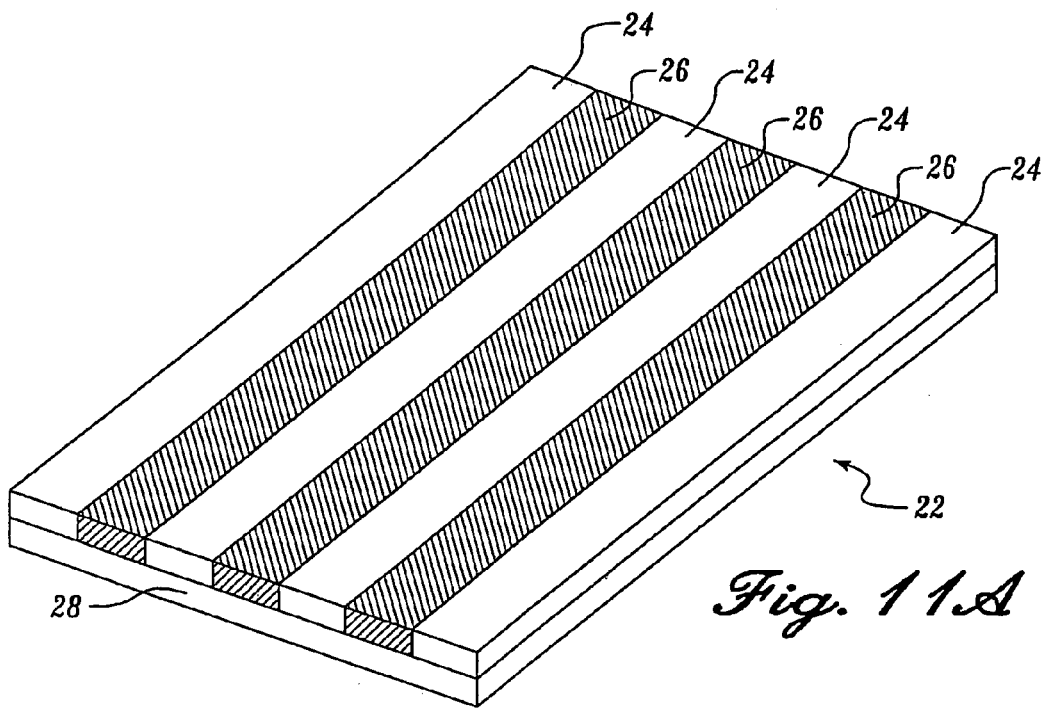
FIG. 11A is a perspective view of another representative composite formed in accordance with the present invention.

Referring to FIG. 11A, fluted absorbent composite 22 includes distribution zones 26 that serve to rapidly acquire and distribute liquid to storage zones 24 and storage core 28. As noted above, distribution zones 26 are composed primarily of fibrous materials, and storage zones 24 and core 28 are generally fibrous layers that include absorbent material. As described above, composite 22 can be formed by attaching bands of fibrous materials and absorbent materials to a storage core to form distribution zones 26 and storage zones 24, respectively. Alternatively, storage zones 24 can be formed integrally with storage core 28 and, similarly, distribution zones 26 can also be integrally formed with storage zones 24 and core 28. Although the distributions zones are generally prepared from wet-laid composites, the absorbent material containing storage zones can be made from air-laid composites. In one preferred embodiment, the distribution zones are formed from wet-laid fibrous composite that include fibrous materials suitable for liquid acquisition and distribution, and the storage zones and core are formed from air-laid fibrous composites that include absorbent material suitable for liquid storage. In another preferred embodiment, the storage zones and core are formed from a wet-laid composite. Generally, an absorbent composite having such a structure has enhanced liquid acquisition compared to conventional storage cores and those having relatively poor fluid communication between composite components.

Figure 11B:
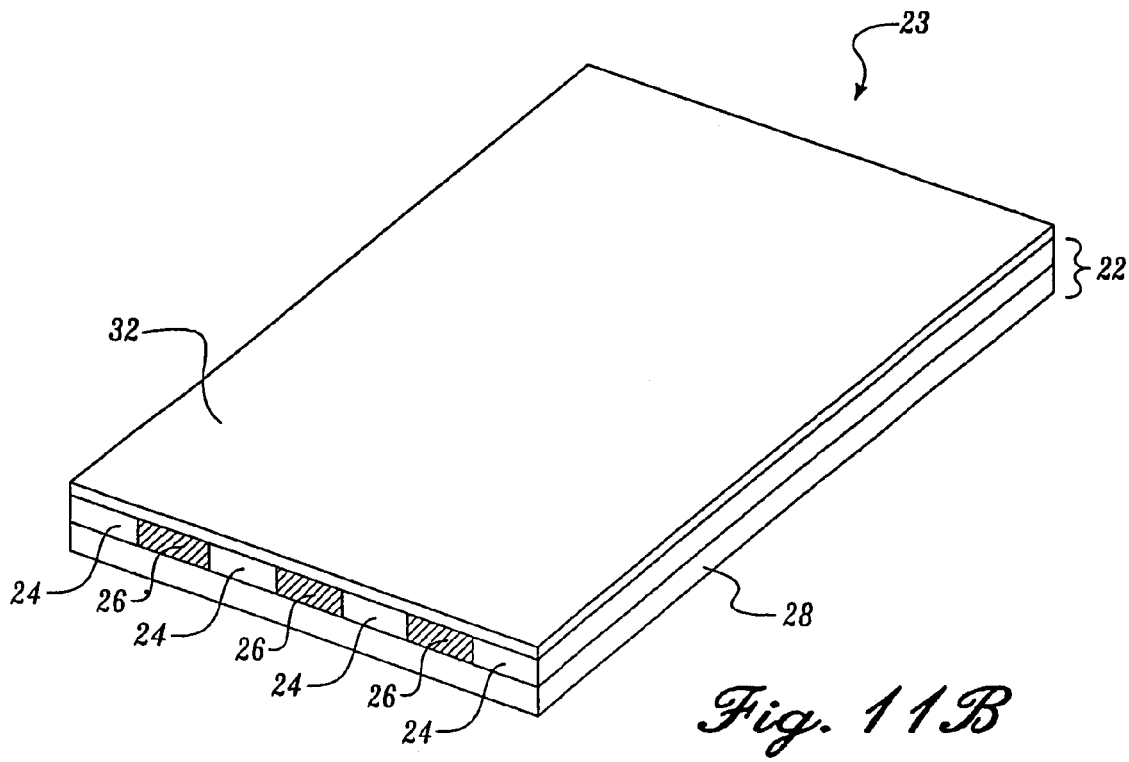
FIG. 11B is a perspective view of an absorbent construct composed of the composite shown in FIG. 11A and an acquisition layer.

Multilayered absorbent constructs can also include the fluted absorbent composite. One such construct is illustrated in FIG. 11B. Referring to FIG. 11B, absorbent construct 23 includes fibrous composite 22 and an acquisition layer 32 (e.g., formed primarily from fibrous materials). As noted above composite 22 includes distribution zones 26, storage zones 24, and storage core 28.

Fluted composites having a unitary structure are generally preferred because of the intimate fluid communication between components (i.e., regions of the composite) and for reasons relating to manufacturability. Accordingly, in a preferred embodiment, the fluted absorbent composite is an integrally formed unitary structure.

The fluted absorbent composite can be formed by wet-laid and foam-forming processes. These general methodologies are known to those of skill in the pulp processing art.

Preferably, the fluted absorbent composite is prepared from a wet-laid or a foam-forming process. A representative example of a wet-laid process is described in U.S. Pat. No. 5,300,192, issued Apr. 5, 1994, entitled "Wet-Laid Fiber Sheet Manufacturing with Reactivatable Binders for Binding Particles to Fibers", expressly incorporated herein by reference. Wet-laid processes are also described in standard texts, such as Casey, Pulp and Paper, 2nd edition, 1960, volume II, Chapter VIII—Sheet Formation. Representative foam processes useful in forming the composite include those known in the art and include those described in U.S. Pat. Nos. 3,716,449; 3,839,142; 3,871,952; 3,937,273; 3,938,782; 3,947,315; 4,166,090; 4,257,754; and 5,215,627, assigned to Wiggins Teape and related to the formation of fibrous materials from foamed aqueous fiber suspensions, and "The Use of an Aqueous Foam as a Fiber-Suspending Medium in Quality Papermaking," *Foams*, Proceedings of a Symposium organized by the Society of Chemical Industry, Colloid and Surface Chemistry Group, R. J. Akers, Ed., Academic Press, 1976, which describes the Radfoam process, all expressly incorporated herein by reference.

In the method of the present invention, absorbent material is incorporated into the composite during the formation of the composite. Generally, the method for forming the fluted absorbent composite includes depositing absorbent material into a fibrous web, and then drying the web, as necessary, to provide the composite.

In a wet-laid method, absorbent material is preferably applied into a fibrous slurry that has been deposited onto a foraminous support (i.e., a forming wire). In the method, absorbent material is injected into an at least partially dewatered fibrous web formed by depositing a fibrous slurry onto a forming wire. The fibrous slurry preferably includes fibers and wet strength agent in a dispersion medium (e.g., a primarily aqueous medium such as water). The absorbent material can be introduced into the fibrous web as a dry particle or, preferably, as a liquid suspension in an aqueous medium, preferably chilled (e.g., 34–40° F.) water. The absorbent material is generally injected into the partially dewatered fibrous web immediately after the slurry's deposition onto the forming wire. The absorbent material is preferably deposited into the partially dewatered fibrous web (i.e., before dewatering of the web is completed and during the formation of the wet composite where the consistency of the web is increased relative to the slurry and, in any event, prior to the drying stage). After depositing the absorbent material into the partially dewatered fibrous web, the web containing fibers and absorbent material is subjected to further removal of at least a portion of the dispersion medium and water, preferably by vacuum, to provide a wet composite. The wet composite is then dried to provide the absorbent composite.

It is desirable to inhibit liquid absorption by the absorbent material during the web formation process. To inhibit liquid absorption, absorbent material can be added to the at least partially dewatered web as an aqueous suspension in chilled water having a temperature in the range from about 0–5° C., preferably from about 0–3° C., and more preferably about 1° C. Alternatively, the absorbent material can be cooled to below 0° C., by placement or storage in a conventional freezer, and then forming a suspension in water, preferably chilled water, immediately prior to web formation. Limiting the period of time that the absorbent material is in contact with liquid during the forming process also has a positive effect on limiting absorbent material liquid absorption. Preferably, the absorbent material suspension is added to the at least partially dewatered fibrous web within about 10 seconds, and more preferably within about 5 seconds after preparing the suspension.

By limiting the liquid absorption by the absorbent material during the formation process, web drying energy and/or time, and the consequent associated expense can be greatly reduced. This advantage can result in web formation processes that are more cost effective and can represent significant savings for consumer absorbent products such as diapers, feminine care products, and adult incontinence products.

As described above, the absorbent composite includes bands of absorbent material that are spaced laterally across the composite's width and that extend longitudinally along the composite's length in the machine direction of the composite. Such a configuration of bands can be achieved by various methods including injecting absorbent material into the fibrous web, which has been at least partially dewatered, through openings or nozzles spaced laterally across the width of the web. The nozzles are connected to an absorbent material supply. The nozzles can be positioned in various configurations and have orifices of varying size to provide bands having various configurations including, for example, various widths. The absorbent material is preferably deposited as a suspension in chilled water. For aqueous suspensions, the absorbent material is injected as a stream or jet into the partially dewatered fibrous web. Injection of the stream can result in significant mixing of the absorbent material and the fibers of the web. The degree of mixing can be controlled by several factors including stream velocity, web velocity, angle of injection, and position of injection relative to the deposition of fibrous slurry on the support, among others. Generally, the closer the absorbent material injection to the point at which dewatering of the fibrous web commences, the greater the mixing of absorbent material and fibers. Also, the greater the mixing of absorbent material and fibers, the lesser the resulting concentration gradient of absorbent material in the composite.

Because the bands of absorbent material can be formed in the composite by deposition or injection through individual nozzles, the nature and characteristics of the flutes that are ultimately formed in the composite can be controlled. For example, referring to the composite illustrated in FIG. 3, the outermost flutes contain absorbent material in relatively greater amounts compared to the inner flutes. Such a composite can be formed by depositing greater concentrations of absorbent material, depositing absorbent material at a greater rate, or utilizing nozzles having larger diameter orifices for the outermost positions. As noted above, absorbent materials having different absorptive and retentive capacities can be selectively deposited in the bands.

The deposition of individual bands also allows for the formation of bands that can include materials in addition to absorbent material. For example, additional fibers can also be introduced into the deposited slurry through the use of these nozzles. Consequently, flutes having additional fibers, including fibers different from the deposited fibrous slurry, can be incorporated into the composite. In one preferred embodiment, the absorbent composite includes bands of absorbent material that further include additional fibers such as, for example, hardwood fibers and/or synthetic fibers. The use of different fibers can be used to form flutes having, for example, higher relative basis weights; greater bulk and softness; increased wicking; and increased rewet performance. Thus, the composite's flutes can be formed from completely different components compared to the base composite (i.e., the initially deposited fibrous slurry).

The composite's absorbent material enriched regions can be stabilized to enhance the structural integrity of the band or flute. Flute integrity can be enhanced by depositing, in addition to absorbent material, a wet strength agent (e.g., Kymene®) and/or fibrous materials including, for example, microfibrillated cellulose and fibrous superabsorbent materials. Fibrous superabsorbent materials are described in U.S. Pat. No. 5,607,550, expressly incorporated herein by reference.

The advantage of versatility allows for the design and formation of various fluted absorbent composites. For example, the base composite can be designed for strength and wicking, while the deposited bands can be designed to maximize swelling and absorbent capacity and to minimize rewet. More specifically, for an absorbent composite that maximizes absorbent capacity, strength, and total material utilization, the base composite can include a mixture of southern pine fibers, eucalyptus fibers, crosslinked fibers and wet strength agent, and the bands can include a mixture of absorbent material and crosslinked cellulosic fibers or the fibers. For a composite having increased capacity and enhanced wicking to the absorbent material, the base composite can include a mixture of southern pine fibers, eucalyptus fibers, and wet strength agent, and the bands can include a mixture of absorbent material, crosslinked cellulosic fibers, and microfibrillated cellulose. Another preferred absorbent composite includes a base composite composed of a refined mixture of crosslinked cellulosic fibers and eucalyptus fibers, and includes bands composed of a mixture of absorbent material and unrefined crosslinked fibers. To reduce rewet, synthetic fibers (e.g., PET fibers) can be introduced into the composite by depositing these fibers into the bands with absorbent material or including some absorbent material in the composite's distribution zones. The versatility of the method of the present invention enables the creation of fluted absorbent composites having a variety of compositions and absorbent properties.

The method of the present invention also allows for the deposition of foam dispersions as bands of materials into a fibrous slurry. In one embodiment, the composite has a wet-laid fibrous base and foam-formed bands. In another embodiment, the composite includes a foam-formed fibrous base and wet-laid bands and, in still another embodiment, the composite includes a foam-formed fibrous base and bands. The ability to deposit a foam dispersion enables the use of a wide range of fiber types, lengths, and deniers in the composite's absorbent bands. By selection of fibers, the bands (and ultimately the composite's flutes) can be, for example, soft and have a degree of stretch. By forming a composite having stretch capabilities, a shaped core can be formed from a rectangular composite, thus eliminating the need to shape the core by cutting, which results in material waste. Such a core also has the greatest density of absorbent material in the crotch area, the site of liquid insult.

As noted above, the absorbent composite can be formed from a combination of fibers, and optionally wet strength agent, in a dispersion medium, and absorbent material. In one embodiment, a fibrous slurry is formed by directly combining fibers, and optionally wet strength agent, in a dispersion medium followed by the addition of absorbent material, preferably as a liquid suspension of chilled water, to an at least partially dewatered fibrous web on a foraminous support. In another embodiment, absorbent material is added to the partially dewatered fibrous web on a foraminous support in combination with fibers as a slurry containing fibers and absorbent material. Such a slurry can be prepared by first combining fibers with a dispersion medium to which is then added absorbent material in a second step.

Once the fibrous slurry is deposited onto the foraminous support, the dispersion medium begins to drain from the deposited slurry to provide an at least partially dewatered fibrous web. Removal of the dispersion medium (e.g., water)

from the deposited fibrous slurry (i.e., the partially dewatered web) continues through, for example, the application of pressure, vacuum, and combinations thereof, and results in the formation of a wet composite.

The absorbent composite is ultimately produced by drying the wet composite. Drying removes at least a portion of the remaining dispersion medium and water and provides an absorbent composite having the desired moisture content. Suitable composite drying methods include, for example, the use of drying cans, air floats and through air dryers. Other drying methods and apparatus known in the pulp and paper industry may also be used. Drying temperatures, pressures and times are typical for the equipment and methods used, and are known to those of ordinary skill in the art in the pulp and paper industry.

For foam methods, the fibrous slurry is an aqueous or foam slurry that further includes a surfactant. Suitable surfactants include ionic, nonionic, and amphoteric surfactants known in the art.

The deposition of the components of the absorbent composite onto the foraminous support ultimately results in the formation of a wet composite that includes absorbent material that may have absorbed water and, as a result, swollen in size. Water is withdrawn from the wet composite containing the water-swollen absorbent material distributed on the support and the wet composite dried.

In the methods of the present invention, the absorbent material preferably absorbs less than about 20 times its weight in the dispersion medium, more preferably less than about 10 times, and even more preferably less than about 5 times its weight in the dispersion medium. Other preferable absorbent materials include materials that absorb liquid only after prolonged contact with liquid, or that absorb liquid only under certain conditions, and do not absorb any significant amount of liquid during the forming process.

Foam methods are advantageous for forming the absorbent for several reasons. Generally, foam methods provide fibrous webs that possess both relatively low density and relatively high tensile strength. For webs composed of substantially the same components, foam-formed webs generally have densities greater than air-laid webs and lower than wet-laid webs. Similarly, the tensile strength of foam-formed webs is substantially greater than for air-laid webs and approach the strength of wet-laid webs. Also, the use of foam-forming technology allows better control of the orientation and uniform distribution of fibers and the incorporation of a wide range of materials (e.g., long and synthetic fibers that cannot be readily incorporated into wet-laid processes) into the composite.

One machine for implementing the method of the present invention is a conventional papermaking machine (wet-laid pulp machine) that has been modified to include a plurality of nozzles positioned downstream from the headbox outlet. Generally, the nozzles are spaced laterally at intervals, for example, regular intervals, across the width of the web. As described above, the nozzles are connected to an absorbent material supply and, in a preferred embodiment, a chilled aqueous suspension of absorbent material is pumped to the nozzles to form an aqueous stream or jet that impinges on and penetrates the surface of the deposited fibrous slurry (i.e., partially dewatered web) as the wet composite is formed. Because the wet composite is moving away from the headbox as it is formed, bands of absorbent material are created in the composite along the machine direction. Through the use of vacuum, the machine drains water from the composite. The wet composite is then dried to provide the final product. A diagrammatic view of a representative machine and method for forming the fluted absorbent composite is illustrated in FIG. 12A.

Figure 12A:
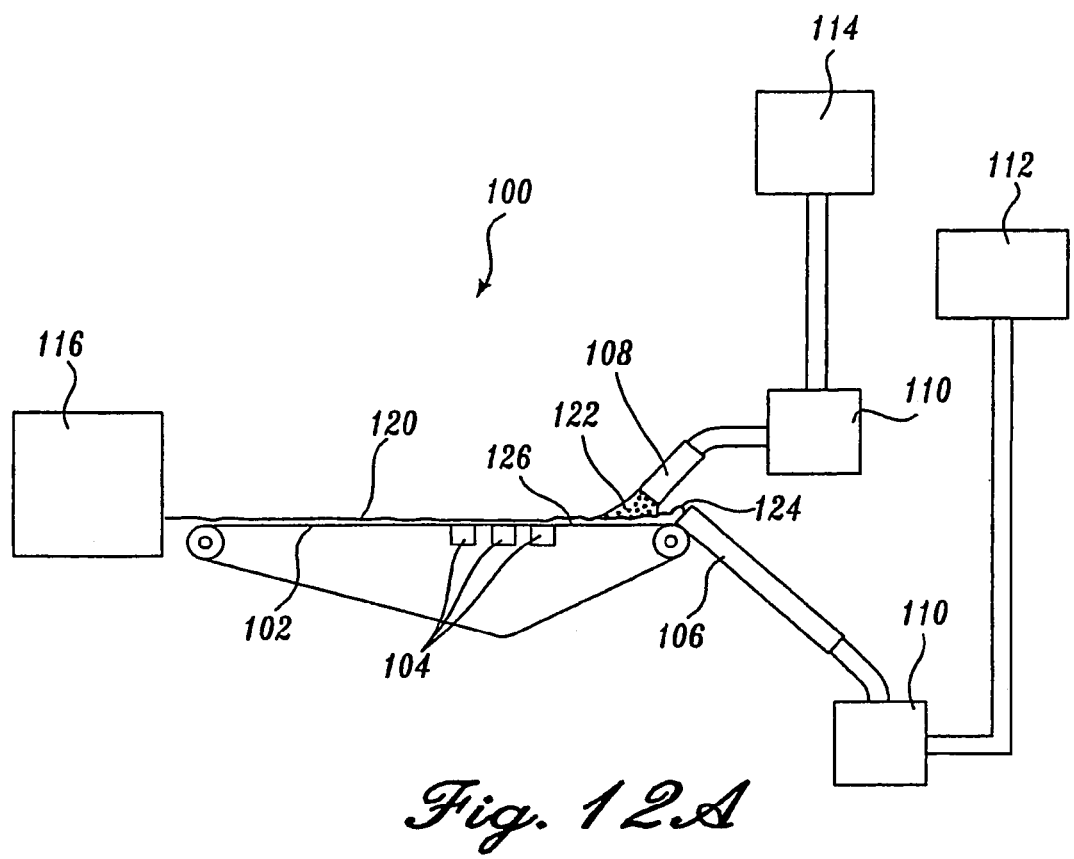
FIG. 12A is a diagrammatic view illustrating a device and method for forming the composite of the present invention.
Figure 12B:
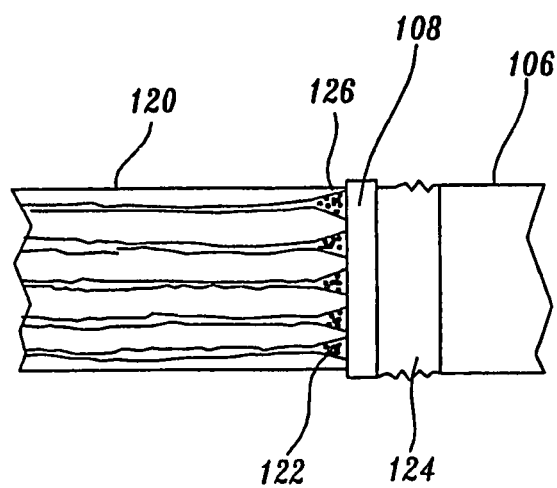
FIG. 12B is a top plan view of a portion of a device for forming the composite of the present invention.

Referring to FIG. 12A, machine 100 includes foraminous support 102 (i.e., a forming wire); vacuum heads 104 for dewatering fibrous slurry 124 to provide wet composite 120; headbox 106 for depositing the fibrous slurry onto support 102; nozzle manifold 108 for injecting absorbent material 122, preferably as an aqueous suspension, into partially dewatered web 126; fibrous slurry supply 112; absorbent material supply 114; pumps 110 for delivering the fibrous slurry and absorbent material from their respective supplies to headbox 106 and manifold 108, respectively; and drying means 116. Briefly, fibrous slurry 124 is deposited from headbox 106 onto support 102 and dewatered to provide partially dewatered web 126. Absorbent material 122, preferably as an aqueous suspension, is injected through nozzle manifold 108 into partially dewatered web 126, preferably prior to extensive dewatering at vacuum heads 104. As described above, manifold 108 includes a plurality of nozzles positioned across the width of support 102 (i.e., the cross-machine direction) to deliver and inject absorbent material in bands across the composite's width. Wet composite 120 is further dewatered along support 102 and then dried by drying means 116 (e.g., heated cans, drying oven, through-air dryer). A top plan view of the injection of absorbent material into the fibrous slurry is illustrated in FIG. 12B.

Figure 13:
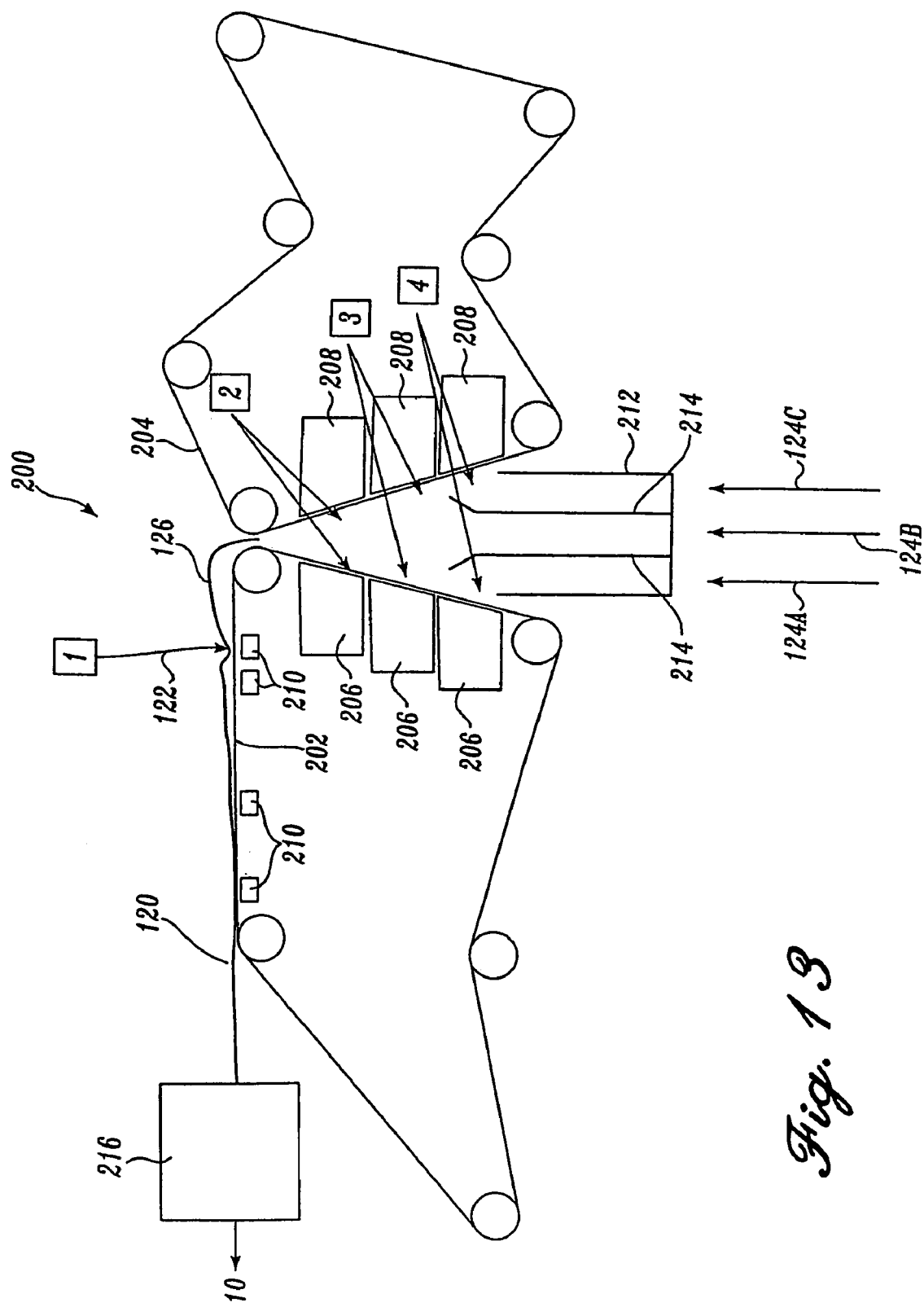
FIG. 13 is a diagrammatic view illustrating a twin-wire device and method for forming the composite of the present invention.

The absorbent composite can be formed by devices and processes that include a twin-wire configuration (i.e., twin-forming wires). A representative twin-wire machine for forming composites is shown in FIG. 13. Referring to FIG. 13, machine 200 includes twin-forming wires 202 and 204 onto which the composite's components are deposited. Basically, fibrous slurry 124 is introduced into headbox 212 and deposited onto forming wires 202 and 204 at the headbox exit. Vacuum elements 206 and 208 dewater the fibrous slurries deposited on wires 202 and 204, respectively, to provide partially dewatered webs that exit the twin-wire portion of the machine as partially dewatered web 126. Web 126 continues to travel along wire 202 and continues to be dewatered by additional vacuum elements 210 to provide wet composite 120 which is then dried by drying means 216 to provide composite 10.

Absorbent material can be introduced into the fibrous web at any one of several positions in the twin-wire process depending on the desired product configuration. For example, absorbent material can be introduced after the partially dewatered fibrous web has exited the twin-wire portion of the machine and has traveled along wire 202. Referring to FIG. 13, absorbent material 122 can be injected into partially dewatered fibrous web 126 at position 1. Alternatively, absorbent material can be introduced into the partially dewatered fibrous web prior to the web exiting the twin-wire portion of the machine (i.e., in the headbox). Referring to FIG. 13, absorbent material 122 can be injected into the partially dewatered web at positions 2, 3, or 4, or other positions along wires 202 and 204 where the web has been at least partially dewatered. Absorbent material can be introduced into the partially dewatered web formed and traveling along wire 202 and/or 204. As noted above, to form the composite having bands of absorbent material extending in the composite's machine direction, absorbent material is injected into the partially dewatered fibrous webs by nozzles spaced laterally across the width of the web. The nozzles are connected to an absorbent material supply. The nozzles can be positioned in various positions (e.g., positions 1, 2, or 3 in FIG. 13) as described above. For example, referring to FIG. 13, nozzles can be located at positions 2 to inject absorbent material into partially dewatered webs on wires 202 and 204. Generally, the extent of mixing of fibers with absorbent material decreases as the fibrous web is dewatered (e.g., less mixing at position 1 than at position 2, and less mixing at position 2 than at position 3).

Depending on the position of absorbent material introduction, the twin-wire method for forming the composite can provide a composite having a fibrous stratum. Representative composites having fibrous strata formed by the twin-wire method of the present invention are shown in FIGS. 14A–H. Referring to FIG. 14A, representative composites 10 include regions 12 enriched with absorbent material, distribution zones 14 substantially free of absorbent material, and fibrous strata 11 coextensive with the outward surfaces of composite 10.

Referring to FIG. 14A, composite 10 can be formed by a method that introduces absorbent material into a single partially dewatered web (i.e., a web traveling on wire 202 or 204). FIGS. 14B and 14C depict similarly formed composites having absorbent material extending into the composite to relatively greater depths (i.e., z-direction penetration). Referring to FIG. 14D, composite 10 includes absorbent material introduced into the center fibrous. Such a composite can be formed by adjusting the depth of absorbent material penetration by, for example, nozzle distance from the forming wire or absorbent material injection angle.

Alternatively, the composite can be formed by a twin-wire method that introduces absorbent material into both partially dewatered webs (i.e., webs traveling on wires 202 and 204). Such a method includes a two sets of nozzles, a first nozzle set for injection into one partially dewatered web, and a second nozzle set for injection into the other partially dewatered web. Referring to FIG. 14E, composite 10 includes regions enriched with absorbent material that extend substantially throughout the composite's depth (i.e., z-direction). Such a composite configuration can be formed from a pair of nozzle sets that are either positioned or timed to provide absorbent material bands that align in the z-direction. Offsetting one set of nozzles from the other, or providing nonsynchronous absorbent material pulses from a pair of aligned nozzle sets, provides composites having offset bands of absorbent material. Such a composite configuration is illustrated in FIG. 14F. FIGS. 14G and 14H illustrate composites formed by methods similar to those which provide the composites shown in FIGS. 14E and 14F, respectively, but in contrast to those composites, the composites of FIGS. 14G and 14H are formed by the introduction of absorbent material to a penetration depth less than that of the composites in FIGS. 14E and 14F.

As shown in FIG. 14, the composite can include integrated phases having fibrous strata coextensive with the outward surfaces of the composite. These fibrous composites can be formed from multilayered inclined formers or twin-wire formers with sectioned headboxes. These methods can provide stratified or phased composites having strata or phases having specifically designed properties and containing components to attain composites having desired properties. The composite's regions of enriched absorbent material (i.e., the composite's absorbent bands) can be located throughout the z-direction by adjusting the basis weights of the upper and lower strata.

Basically, the position of the absorbent material band in the composite's z-direction effectively defines the fibrous stratum covering the band. For a formation method that includes a single fiber furnish, the band position can be adjusted by positioning the absorbent material injection system (e.g., nozzle set) in relation to the forming wire. For methods that include multiple furnishes, the upper and lower strata can be composed of the same or different components and introduced into a sectioned headbox.

Referring to FIGS. 13 and 14A, composite 10 having strata 11 can be formed by machine 200. For composites in which strata 11 comprise the same components, a single fiber furnish 124 is introduced into headbox 212. For forming composites having strata 11 comprising different components, headbox 212 includes one or more baffles 214 for the introduction of fiber furnishes (e.g., 124a, 124b, and 124c) having different compositions. In such a method, the upper and lower strata can be formed to include different components and have different basis weights and properties.

Preferably, the fluted composite is formed by a foam-forming method using the components described above. In the foam-forming method, fibrous webs having multiple strata and including bands of absorbent material can be formed from multiple fibrous slurries. In a preferred embodiment, the foam-forming method is practiced on a twin-wire former.

The method can provide a variety of multiple strata composites including, for example, composites having three strata. A representative composite having three strata includes a first stratum formed from fibers (e.g., synthetic fibers, cellulosic, and/or binder fibers); an intermediate stratum formed from fibers and/or other absorbent material such as superabsorbent material; and a third stratum formed from fibers. The method of the invention is versatile in that such a composite can have relatively distinct and discrete strata or, alternatively, have gradual transition zones from stratum-to-stratum.

A representative method for forming a fibrous web having an intermediate stratum generally includes the following steps:
  (a) forming a first foam fibrous slurry comprising fibers and a surfactant in an aqueous dispersion medium;
  (b) forming a second foam fibrous slurry comprising fibers and a surfactant in an aqueous dispersion medium;
  (c) moving a first foraminous element (e.g., a forming wire) in a first path;
  (d) moving a second foraminous element in a second path;
  (e) passing the first foam slurry into contact with the first foraminous element moving in a first path;
  (f) passing the second foam slurry into contact with the second foraminous element moving in the second path;
  (g) passing a third material between the first and second foam slurries such that the third material does not contact either of the first or second foraminous elements; and
  (h) forming a fibrous web from the first and second foam slurries and third material by withdrawing foam and liquid from the slurries through the first and second foraminous elements.

As noted above, the method is suitably carried out on a twin-wire former, preferably a vertical former, and more preferably, a vertical downflow twin-wire former. In the vertical former, the paths for the foraminous elements are substantially vertical.

Figure 15:
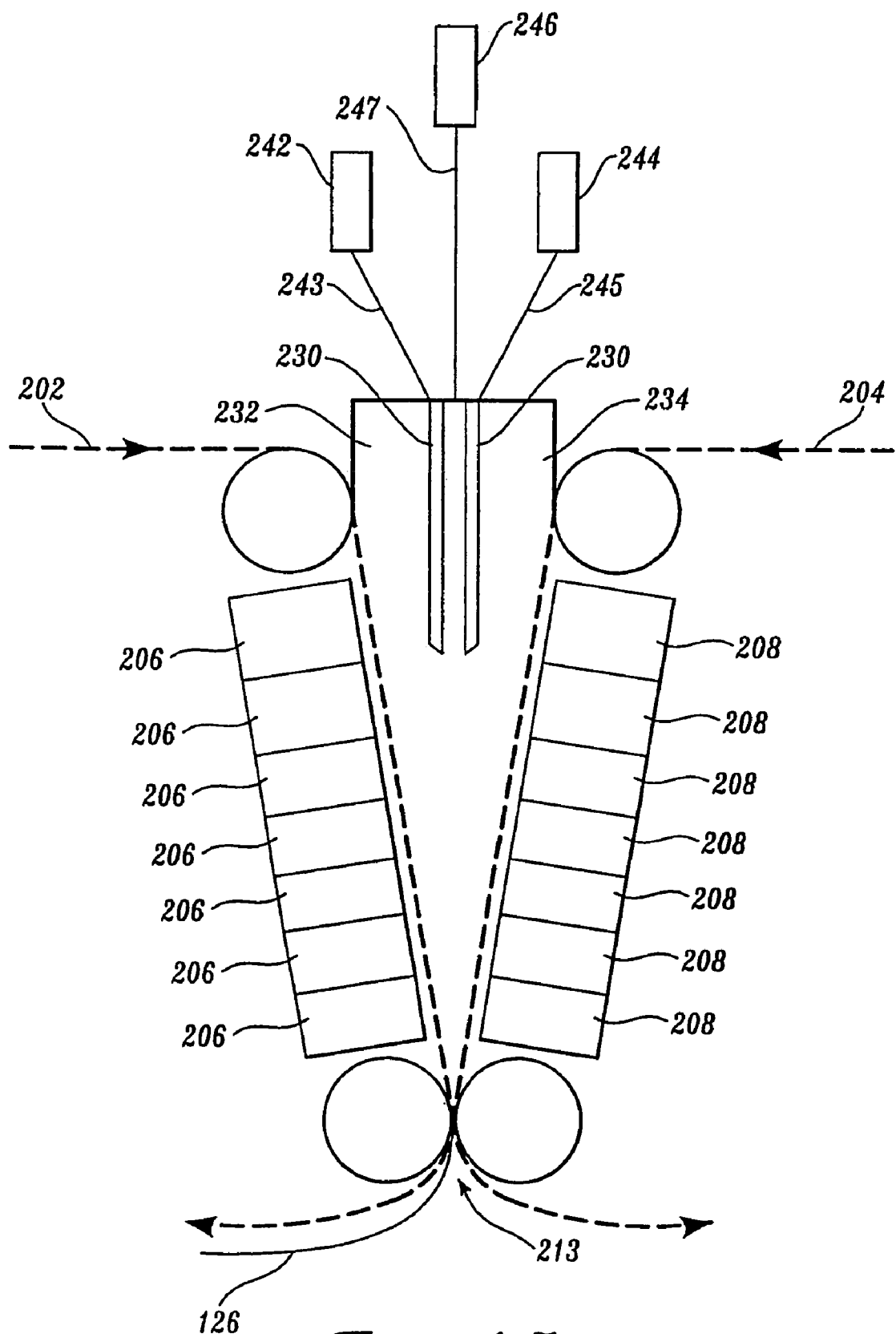
FIG. 15 is a diagrammatic view illustrating a representative headbox assembly and method for forming the composite of the present invention.

A representative vertical downflow twin-wire former useful in practicing the method of the invention is illustrated in FIG. 15. Referring to FIG. 15, the former includes a vertical headbox assembly having a former with a closed first end (top), closed first and second sides and an interior volume. A second end (bottom) of the former is defined by moving first and second foraminous elements, 202 and 204, and forming nip 213. The interior volume defined by the former's closed first end, closed first and second sides, and first and second foraminous elements includes an interior structure 230 extending from the former first end and toward the second end. The interior structure defines a first volume 232 on one side thereof and a second volume 234 on the other side thereof. The former further includes supply 242 and means 243 for introducing a first fiber/foam slurry into the first volume, supply 244 and means 245 for introducing a second fiber/foam slurry into the second volume, and supply 246 and means 247 for introducing a third material into the interior structure. Means for withdrawing foam (e.g., suction boxes 206 and 208) from the first and second slurries through the foraminous elements to form a web are also included in the headbox assembly.

In the method, the twin-wire former includes a means for introducing at least a third material through the interior structure in such a way that the third material forms bands or stripes in the resulting web. Preferably, the introducing means include at least a first plurality of conduits having a first effective length. A second plurality of conduits having a second effective length different from the first length may also be used. More than two sets of conduits can also be used.

Figure 16:
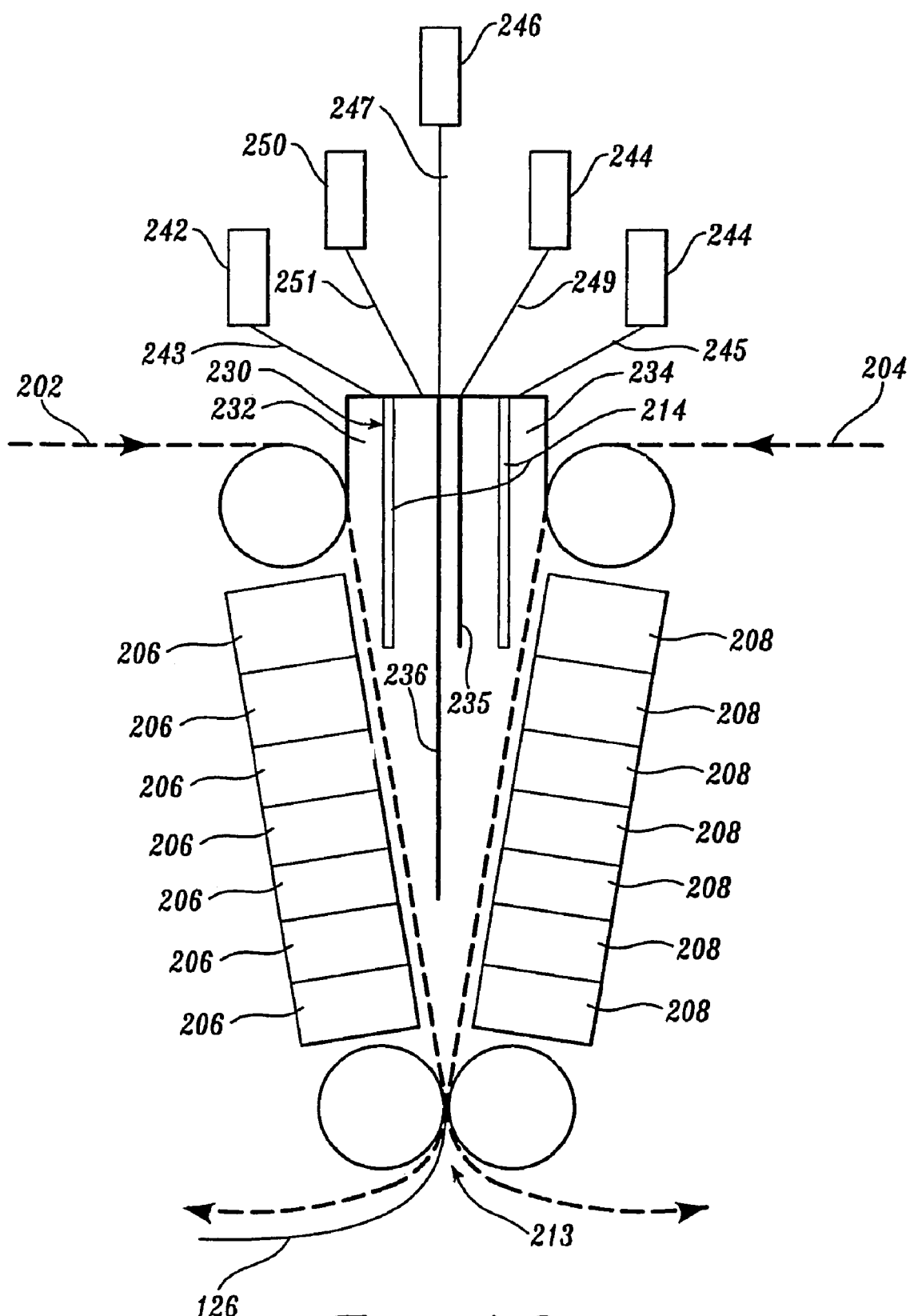
FIG. 16 is a diagrammatic view illustrating a representative headbox assembly and method for forming the composite of the present invention.

Another representative vertical downflow twin-wire former useful in practicing the method of the invention is illustrated in FIG. 16. Referring to FIG. 16, the former includes a vertical headbox assembly having an interior volume defined by the former's closed first end, closed first and second sides, and first and second foraminous elements, 202 and 204, and includes an interior structure 230 extending from the former first end and toward the second end. In this embodiment, interior structure 230 includes plurality of conduits 235 and 236, and optional divider walls 214.

The interior structure defines a first volume 232 on one side thereof and a second volume 234 on the other side thereof. The former further includes supply 242 and means 243 for introducing a first fiber/foam slurry into the first volume, supply 244 and means 245 for introducing a second fiber/foam slurry into the second volume, supply 246 and means 247 for introducing a third material into plurality of conduits 236, supply 248 and means 249 for introducing a third material into plurality of conduits 235, and supply 250 and means 251 for introducing another material, such as a foam slurry, within the volume defined by walls 214.

Figure 17:
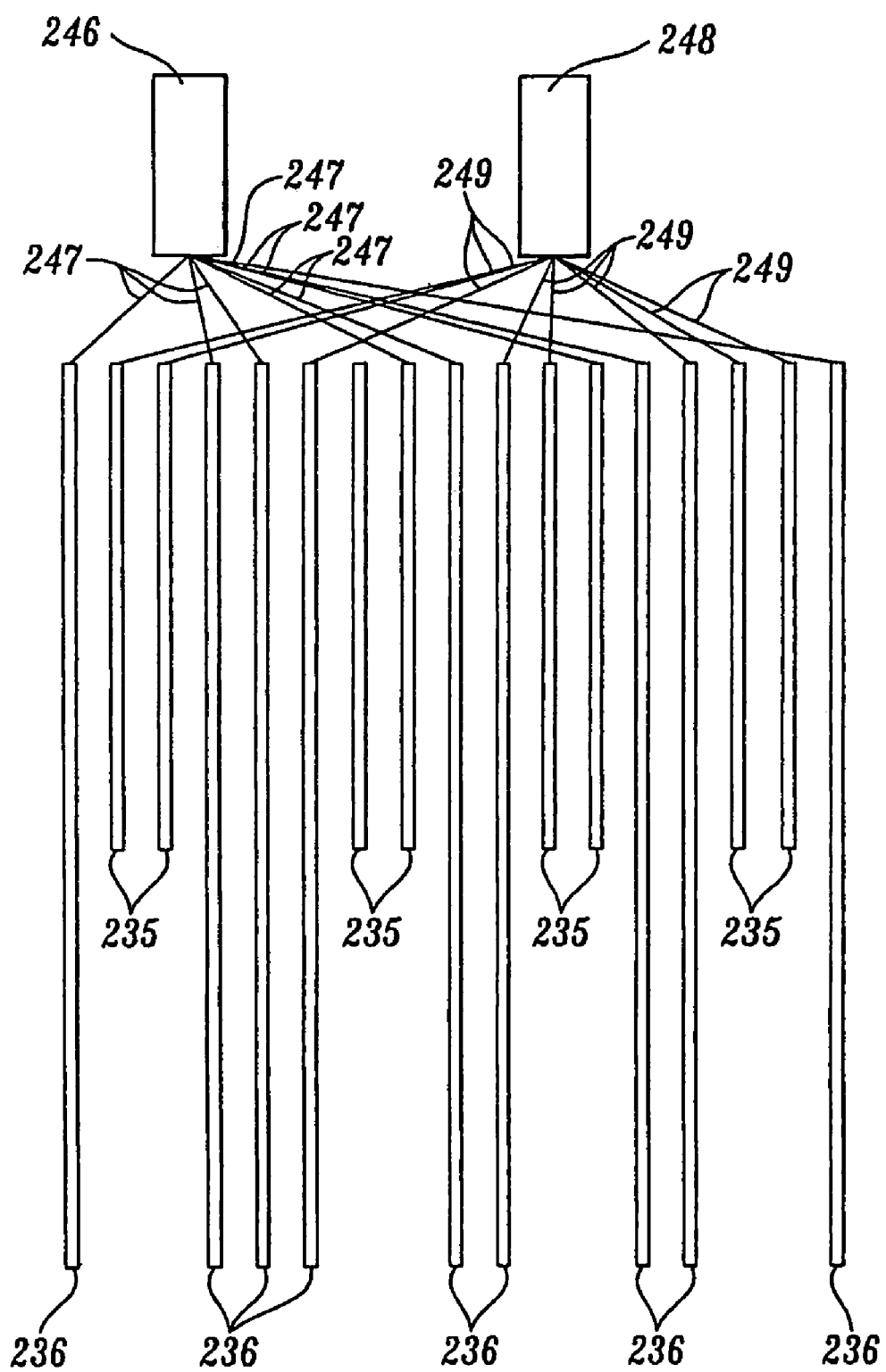
FIG. 17 is a view illustrating representative conduits for introducing absorbent material into a fibrous web in accordance with the present invention.

Plurality of conduits 235 can have an effective length different from plurality of conduits 236. The third material can be introduced through conduits 235 and 236, or, alternatively, a third material can be introduced through conduits 235 and a fourth material can be introduced through conduits 236. Preferably, the ends of conduits 235 and 236 terminate at a position beyond where the suction boxes begin withdrawing foam from the slurries in contact with the foraminous elements (i.e., beyond the point where web formation begins). Plurality of conduits 235 and/or 236 are suitable for introducing stripes or bands of third material in fibrous webs formed in accordance with the present invention. Plurality of conduits 235 and 236 can be moved in a first dimension toward and away from nip 213, and also in a second dimension substantially perpendicular to the first, closer to one forming wire or the other. Representative plurality of conduits 235 and 236 are illustrated in FIG. 17.

Generally, the former's interior structure (i.e., structure 230 in FIGS. 15 and 16) is positioned with respect to the foraminous elements such that material introduced through the interior structure will not directly contact the first and second foraminous elements. Accordingly, material is introduced through the interior structure between the first and second slurries after the slurries have contacted the foraminous elements and withdrawal of foam and liquid from those slurries has commenced. Such a configuration is particularly advantageous for introducing superabsorbent materials and for forming stratified structures in which the third material is a foam/fiber slurry. Depending upon the nature of the composite to be formed, the first and second fiber/foam slurries may be the same, or different, from each other and from the third material.

In a preferred embodiment, the method includes introducing the third material at a plurality of different points to provide a composite having bands or stripes of third material within the product. The positions of at least some of the plurality of different points for introducing the third material into the headbox can be adjusted when it is desired to adjust the introduction point in a first dimension toward and away from the headbox exit (i.e., nip 213 in FIGS. 15 and 16); and to adjust at least some of the plurality of points in a second dimension substantially perpendicular to the first dimension, closer to one forming wire or the other.

The method can also include utilizing a plurality of distinct conduits, the conduits being of at least two different lengths, for introducing the third material into the headbox. The method can also be utilized in headboxes having dividing walls that extend part of the length of the conduits toward the headbox exit. Such headboxes are illustrated in FIGS. 13 and 16.

The means for introducing first and second foam slurries into the first and second volumes can include any conventional type of conduit, nozzle, orifice, header, or the like. Typically, these means include a plurality of conduits are provided disposed on the first end of the former and facing the second end.

The means for withdrawing foam from the first and second slurries through the foraminous elements to form a web on the foraminous elements are also included in the headbox assembly. The means for withdrawing foam can include any conventional means for that purpose, such as suction rollers, pressing rollers, or other conventional structures. In a preferred embodiment, first and second suction box assemblies are provided and mounted on the opposite sides of the interior structure from the foraminous elements (see boxes 206 and 208 in FIGS. 13, 15, and 16).

The fluted absorbent composite can be incorporated as an absorbent core or storage layer in an absorbent article including, for example, a diaper or feminine care product. The absorbent composite can be used alone, or as illustrated in FIGS. 18 and 19, can be used in combination with one or more other layers. FIG. 18 illustrates absorbent construct 30 where composite 10 is employed as a storage layer in combination with an upper acquisition layer 32. As illustrated in FIG. 19 illustrating construct 40, a third layer 42 (e.g., distribution layer) can also be employed, if desired, with composite 10 and acquisition layer 32.

Figure 20:
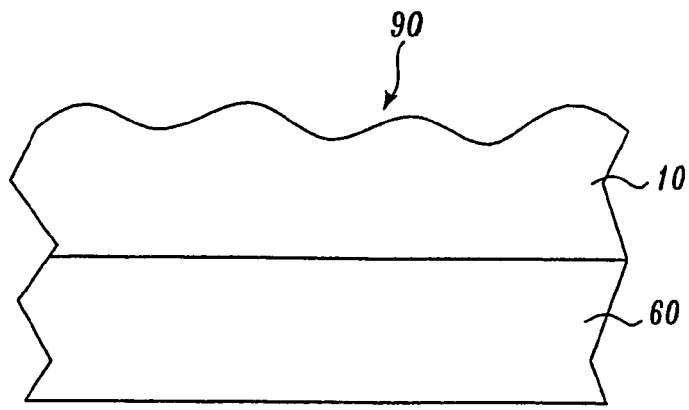
FIG. 20 is a cross-sectional view of a portion of an absorbent construct incorporating a storage layer and a representative composite formed in accordance with the present invention.
Figure 21:
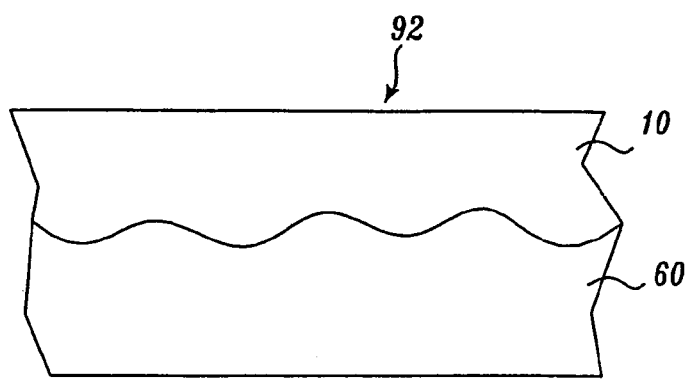
FIG. 21 is a cross-sectional view of a portion of an absorbent construct incorporating a storage layer and a representative composite formed in accordance with the present invention.

The fluted absorbent composite can also be incorporated as a liquid management layer in an absorbent article such as a diaper. In such an article, the composite can be used in combination with a storage core or layer. In the combination, the liquid management layer can have a surface area that is smaller than, the same size as, or slightly greater than the surface area of the storage layer's surface facing the fluted composite. Representative absorbent constructs that incorporate the fluted composite in combination with a storage layer are shown in FIGS. 20 and 21. Referring to FIG. 20, absorbent construct 90 includes fluted composite 10 and storage layer 60. Storage layer 60 is preferably a fibrous layer that includes absorbent material. The storage layer can be formed by any method including air-laid, wet-laid, and foam-forming methods.

For constructs that include a storage layer and the fluted composite as an liquid management layer, the absorbent material in the fluted composite can be the same, similar, or different from the absorbent material in the storage layer.

In certain embodiments, the fluted absorbent composite is asymmetric in that the composite's facing and backing surfaces are not identical. In these embodiments, the composite has a first surface into which absorbent material has been injected and an opposing surface (i.e., machine side) composed substantially of fibers and which constitutes a surface of the composite's fibrous base. For absorbent constructs that contain, in addition to the fluted composite, a storage layer, the composite can be oriented in two ways. In one embodiment, the fluted composite is oriented with its fluted surface directed toward the wearer. A representative construct 90 having a storage layer and fluted composite having its fluted surface directed toward the wearer is shown in FIG. 20. Alternatively, as shown in FIG. 21, representative construct 92 includes composite 10 having the composite's flutes directed toward storage layer 60. The surface of the storage layer may or may not conform to the surface of the fluted composite.

It is anticipated that the rewet of constructs that include the fluted composite can also be reduced by incorporating synthetic fibers (e.g., hydrophobic fibers such as polyester fibers) into the composite's fibrous base. When used in combination with a storage layer, the fluted composite having a fibrous base that includes synthetic (hydrophobic) fibers is preferably incorporated into the construct in the inverted configuration.

Figure 22:
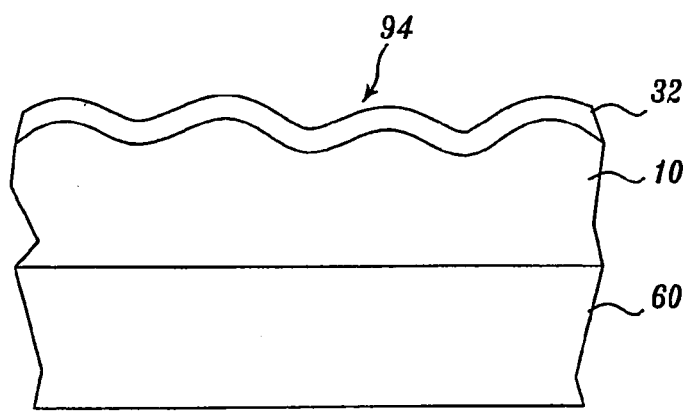
FIG. 22 is a cross-sectional view of a portion of an absorbent construct incorporating a storage layer, an acquisition layer, and a representative composite formed in accordance with the present invention.
Figure 23:
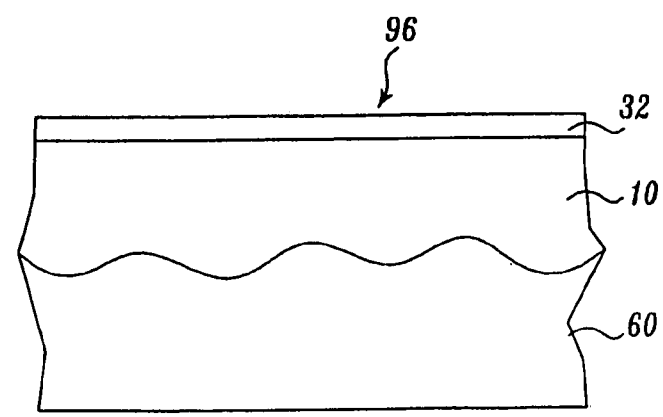
FIG. 23 is a cross-sectional view of a portion of an absorbent construct incorporating a storage layer, an acquisition layer, and a representative composite formed in accordance with the present invention.
Figure 24A:
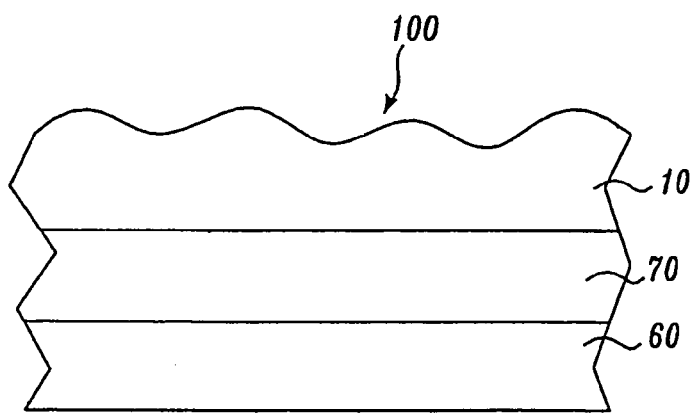
FIGS. 24A–24D are cross-sectional views of a portion of absorbent constructs incorporating a representative composite formed in accordance with the present invention.
Figure 24B:
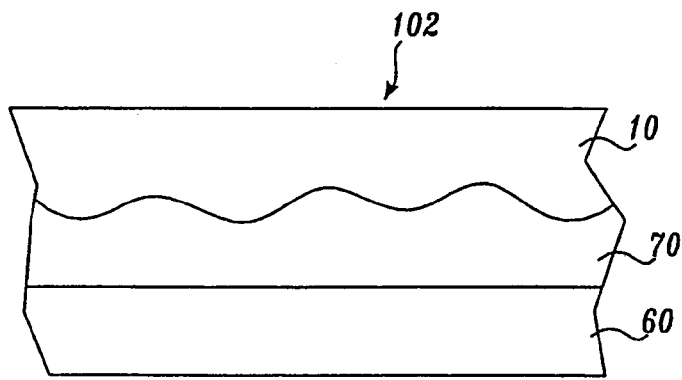
Figure 24C:
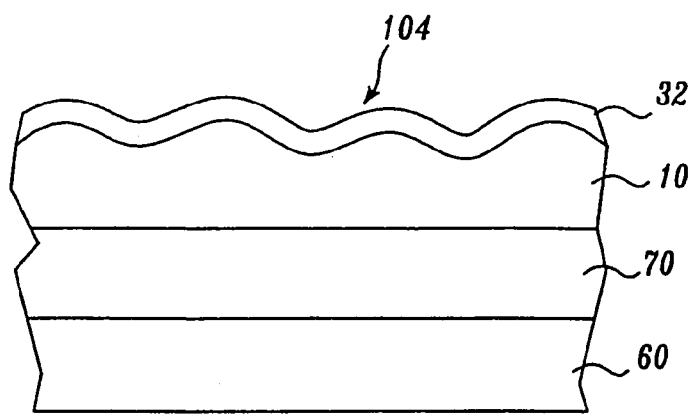
Figure 24D:
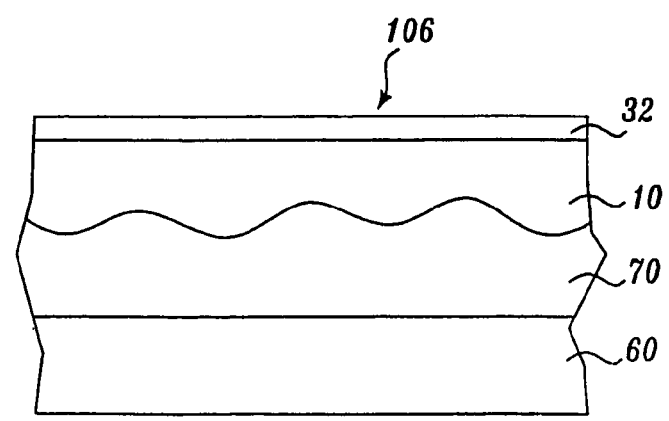
Figure 25A:
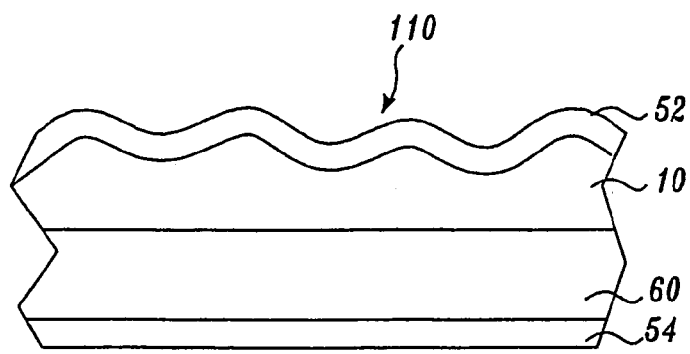
FIGS. 25A–25H are cross-sectional views of a portion of absorbent articles incorporating a representative composite formed in accordance with the present invention.
Figure 25B:
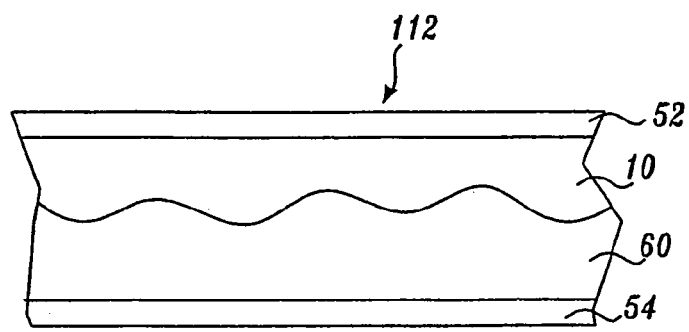
Figure 25C:
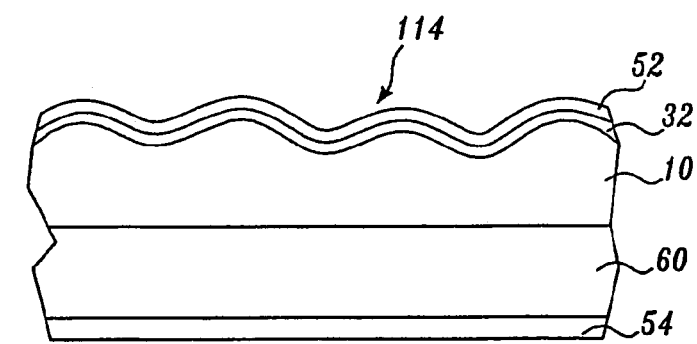
Figure 25D:
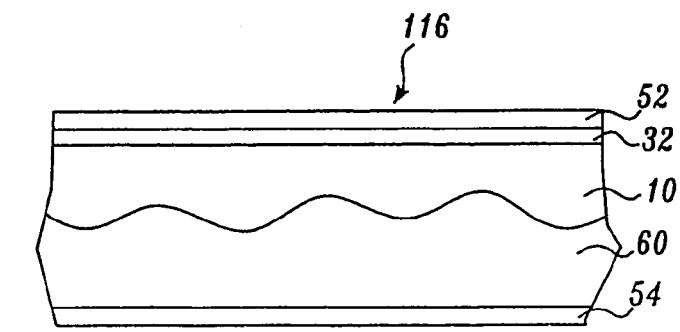
Figure 25E:
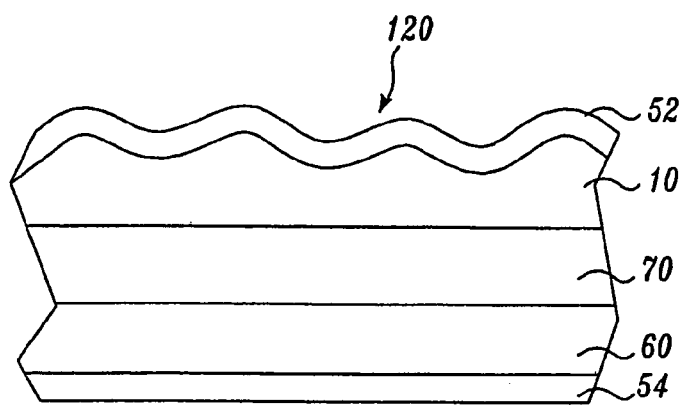
Figure 25F:
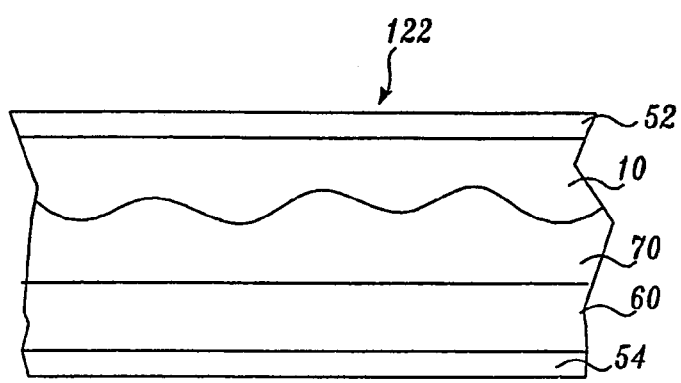
Figure 25G:
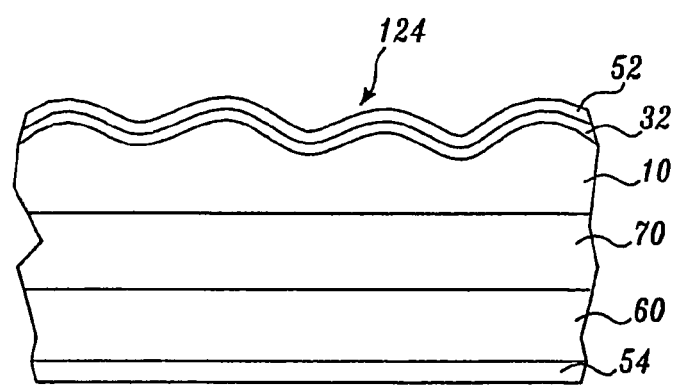
Figure 25H:
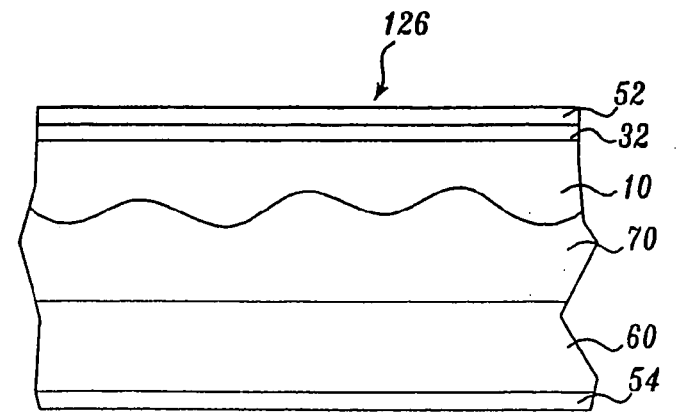

To further enhance rewet performance, an acquisition layer can be combined with the fluted composite and storage layer. FIGS. 22 and 23 illustrate absorbent constructs 94 and 96, respectively, each having acquisition layer 32 overlaying composite 10 and storage layer 60.

Constructs 90, 92, 94, and 96 can further include intermediate layer 70 to provide constructs 100, 102, 104, and 106, shown in FIGS. 24A through 24D, respectively. Intermediate layer 70 can be, for example, a tissue layer, a nonwoven layer, an air-laid or wet-laid pad, or a fluted composite.

Constructs 90, 92, 94, 96, 100, 102, 104, and 106 can be incorporated into absorbent articles. Generally, absorbent articles 110, 112, 114, 116, 120, 122, 124, and 126, shown in FIGS. 25A through 25H, respectively, include a liquid pervious facing sheet 52 and a liquid impervious backing sheet 54 and constructs 90, 92, 94, 96, 100, 102, 104, and 106, respectively. In such absorbent articles, the facing sheet is joined to the backing sheet.

Figure 26A:
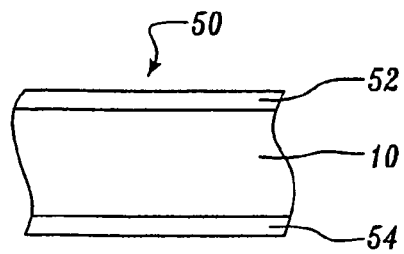
FIG. 26A is a cross-sectional view of a portion of an absorbent article incorporating a representative composite formed in accordance with the present invention.
Figure 26B:
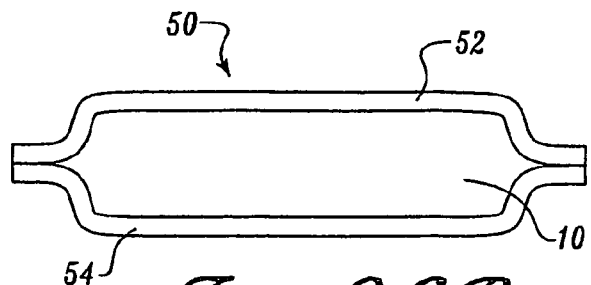
FIG. 26B is a cross-sectional view of a preferred embodiment of an absorbent article incorporating a liquid pervious facing sheet, a liquid impervious backing sheet, and a representative composite formed in accordance with the present invention.
Figure 27:
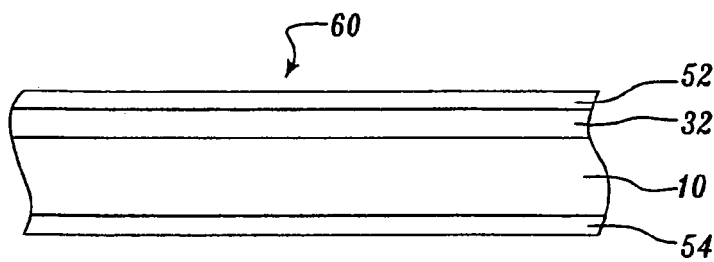
FIG. 27 is a cross-sectional view of a portion of an absorbent article incorporating a representative composite formed in accordance with the present invention.
Figure 28:
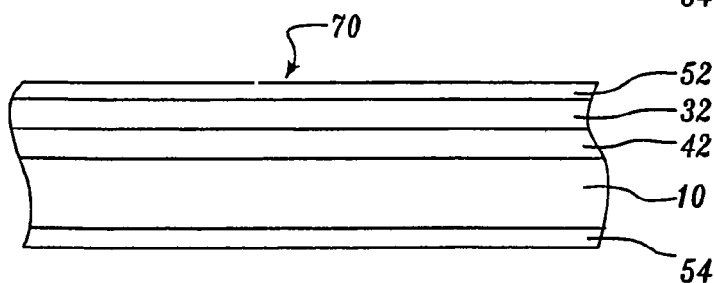
FIG. 28 is a cross-sectional view of a portion of an absorbent article incorporating a representative composite formed in accordance with the present invention.

A variety of suitable constructs can be produced from the absorbent composite. The most common include absorptive consumer products, such as diapers, feminine hygiene products such as feminine napkins, and adult incontinence products. For example, referring to FIGS. 26A and 26B, absorbent article 50 includes absorbent composite 10 and has a liquid pervious facing sheet 52 and a liquid impervious backing sheet 54. As shown in FIG. 26B, facing sheet 52 is joined to backing sheet 54. Referring to FIG. 27, absorbent article 60 includes absorbent composite 10 and an overlying acquisition layer 32. A liquid pervious facing sheet 52 overlies acquisition layer 32, and a liquid impervious backing sheet 54 underlies absorbent composite 10. These absorbent composites will provide advantageous liquid absorption performance for use in, for example, diapers. FIG. 28 illustrates absorbent construct 70, which further includes distribution layer 42 interposed between acquisition layer 32 and composite 10. As described above, the fluted structure of the absorbent composite aids in fluid transport and absorption in multiple wettings.

Figure 29:
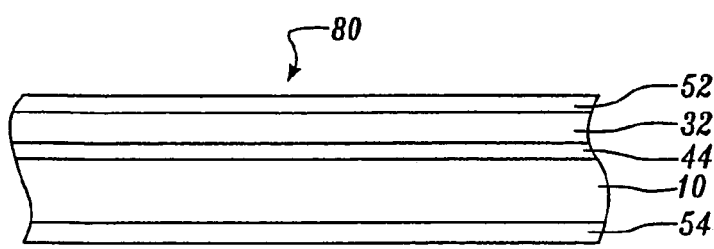
FIG. 29 is a cross-sectional view of a portion of an absorbent article incorporating a representative composite formed in accordance with the present invention.
Figure 30A:
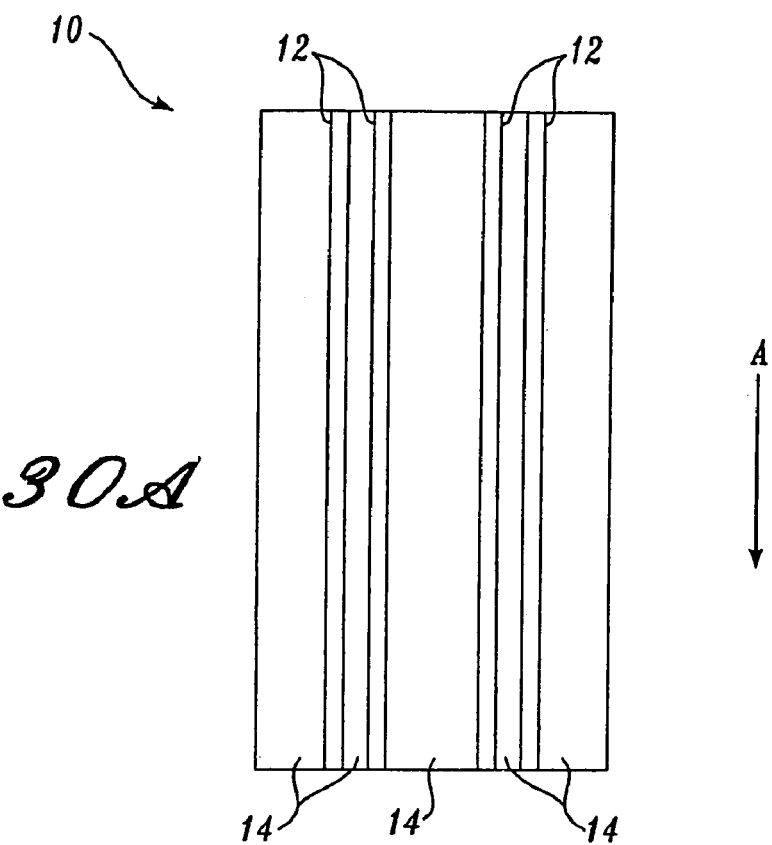
FIG. 30A is a top view of a representative composite formed in accordance with the present invention having bands of absorbent material running the length of the composite in the machine direction and irregularly spaced apart across the width of the composite.
Figure 30B:
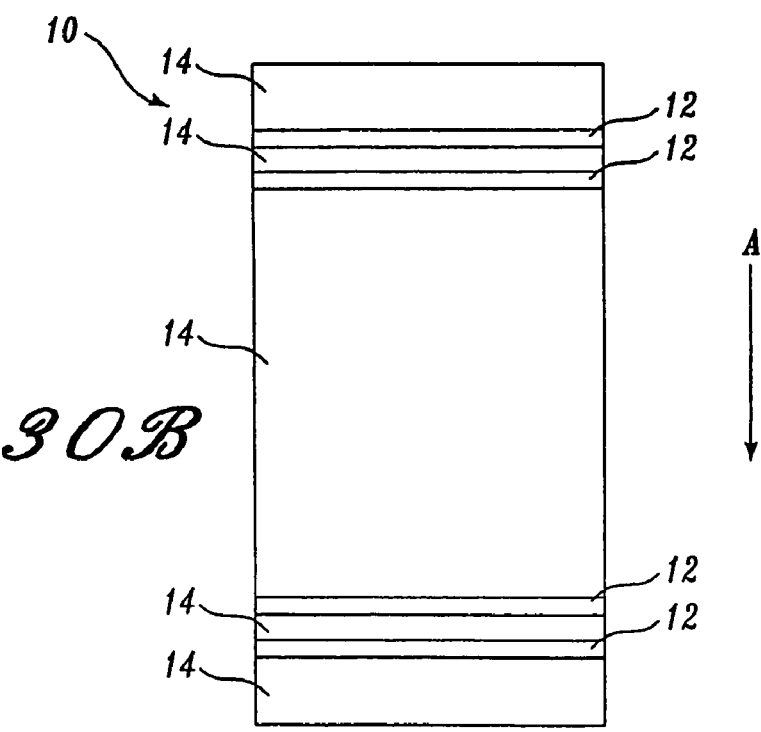
FIG. 30B is a top view of a representative composite formed in accordance with the present invention having bands of absorbent material running across the width of the composite and irregularly spaced along the machine direction of the composite.

One of ordinary skill will be able to make a variety of different constructs using the concepts taught herein. For example, a typical construction of an adult incontinence absorbent structure is shown in FIG. 29. The article 80 includes facing sheet 52, acquisition layer 32, absorbent composite 10, and backing sheet 54. Facing sheet 22 is pervious to liquid while backing sheet 24 is impervious to liquid. In this construct, a liquid pervious tissue 44 composed of a polar, fibrous material is positioned between absorbent composite 10 and acquisition layer 32.

The present invention provides a fibrous absorbent composite containing absorbent material and methods for its formation. The absorbent composite is a fibrous structure that includes absorbent material dispersed in bands along the composite's length. Between the bands of absorbent material, the absorbent composite has continuously open distribution zones that preclude gel blocking in the composite. After initial liquid insult, the composite develops flutes that open the fibrous structure and increase the liquid acquisition rate for subsequent liquid insults. The combination of flutes and distribution zones allows for total utilization of the absorbent composite as a storage core when incorporated into an absorbent article such as a diaper. The fluted absorbent composite can be advantageously used as a liquid management layer or a storage core in absorbent articles such as diapers.

The following examples are provided for the purpose of illustrating, and not limitation, the invention.

EXAMPLES

Example 1

Acquisition Times for a Representative Fluted Absorbent Composite

In this example, the acquisition time for a representative fluted absorbent composite (Composite A) is compared to a commercially available diaper (Diaper A, Kimberly-Clark). Also included in the comparison is an absorbent composite (Composite B) having a composition similar to the composite and composed of fibers (50:50 crosslinked fibers and southern pine pulp fibers), wet strength agent, and absorbent material distributed relatively uniformly throughout the composite. The formation of Composite B is described in provisional U.S. patent application Ser. No. 60/046,395, filed May 13, 1997, and international application Serial No. PCT/US98/09682, filed May 12, 1998, assigned to Weyerhaeuser Company, each expressly incorporated herein by reference.

The tests were conducted on commercially available diapers (Kimberly-Clark) from which the core and surge management layer were removed and used as surrounds for the fluted absorbent composite and for Composite B. The test diapers were prepared by inserting the fluted absorbent composite or Composite B into the diapers.

The aqueous solution used in the tests is a synthetic urine available from National Scientific under the trade name RICCA. The synthetic urine is a saline solution containing 135 meq./L sodium, 8.6 meq./L calcium, 7.7 meq./L magnesium, 1.94% urea by weight (based on total weight), plus other ingredients.

A sample of the absorbent structure is prepared for the test by determining the center of the structure's core, measuring 1 inch to the front for liquid application location, and marking the location with an "X." Once the sample is prepared, the test is conducted by first placing the sample on a plastic base (4¾ inch×19¼ inch) and then placing a funnel acquisition plate (4 inch×4 inch plastic plate) on top of the sample with the plate's hole positioned over the "X". A donut weight (1400 g) is then placed on top of the funnel acquisition plate to which is then attached a funnel (4 inch diameter). Liquid acquisition is then determined by pouring 100 mL synthetic urine into the funnel and measuring the time from when liquid is first introduced into the funnel to the time that liquid disappears from the bottom of the funnel into the sample. The measured time is the acquisition time for the first liquid insult. After waiting 1 minute, a second 100 mL portion is added to the funnel and the acquisition time for the second insult is measured. After waiting an additional 1 minute, the acquisition is repeated for a third time to provide an acquisition time for the third insult. The acquisition times reported in seconds for each of the three successive 100 mL liquid insults for Diaper A, Composite B, and Composite A are summarized in Table 1.

TABLE 1

Acquisition Time Comparison
Acquisition Time (sec)

| Insult | Diaper A | Composite B | Composite A |
|--------|----------|-------------|-------------|
| 1 | 45 | 10 | 10 |
| 2 | 60 | 11 | 6 |
| 3 | 75 | 10 | 4 |

As shown in Table 1, liquid is more rapidly acquired by the absorbent composite than for the commercially available diaper containing an air-laid storage core. The results show that the air-laid core does not acquire liquid nearly as rapidly as the wet-laid composite. The commercial diaper also exhibited characteristic diminution of acquisition rate on successive liquid insults. In contrast, the composite shows a decrease in acquisition time as the composite continued to absorb liquid on successive insult. Significantly, the absorbent composite exhibits an acquisition time for the third insult that is substantially less (about 10-fold) than that of the commercially available diaper for initial insult. The results reflect the greater wicking ability and capillary network for the wet-laid composites compared to conventional air-laid storage cores in general, and the enhanced performance of the fluted absorbent composite in particular.

For the reasons noted above, the observed acquisition time for wet-laid Composite B is also less than for the air-laid core. The acquisition times for Composite B on successive insults remain substantially constant. In contrast, Composite A exhibits a greatly reduced acquisition times on the second and third insults. The increased rate is attributable to the banded nature of the absorbent material in the composite. Thus, the results show that even among wet-laid composites containing absorbent material, the configuration of absorbent material within the composite is a significant factor in liquid acquisition. Whereas homogeneously distributed absorbent material in a wet-laid composite provides advantages over similarly composed air-laid composites, wet-laid composites having bands of absorbent material provide further significant advantages including enhanced and persistent liquid acquisition.

Example 2

Acquisition Rate and Rewet for Representative Fluted Absorbent Composites

In this example, the acquisition time and rewet of representative fluted absorbent composites (designated Composites A1–A4) are compared to a commercially available diaper (Diaper A, Kimberly-Clark). Composites A1–A4 differ by the method by which the composites were dried. Also included in the comparison are a series of absorbent composites (Composites B1–B4) formed as described above for Composite B in Example 1 and differing by the method by which they were dried.

Certain properties of the tested composites including the amount of superabsorbent polymeric material (weight percent SAP) in the composite and basis weight for each of the composites are summarized in Table 2.

The tests were conducted on commercially available diapers (Kimberly-Clark) from which the cores were removed and used as surrounds for the fluted absorbent composites and for Composites B1–B4. The test diapers were prepared by inserting the tested composites into the diapers.

The acquisition time and rewet are determined in accordance with the multiple-dose rewet test described below.

Briefly, the multiple-dose rewet test measures the amount of synthetic urine released from an absorbent structure after each of three liquid applications, and the time required for each of the three liquid doses to wick into the product.

The aqueous solution used in the tests is a synthetic urine available from National Scientific under the trade name RICCA, and as described above in Example 1.

A preweighed sample of the absorbent structure is prepared for the test by determining the center of the structure's core, measuring 1 inch to the front for liquid application location, and marking the location with an "X." A liquid application funnel (minimum 100 mL capacity, 5–7 mL/s flow rate) is placed 4 inches above surface of sample at the "X." Once the sample is prepared, the test is conducted as follows. Flatten the sample, nonwoven side up, onto a table top under the liquid application funnel. Fill the funnel with a dose (100 mL) of synthetic urine. Place a dosing ring (5/32 inch stainless steel, 2 inch ID×3 inch height) onto the "X" marked on the samples. Apply a first dose of synthetic urine within the dosing ring. Using a stopwatch, record the liquid acquisition time in seconds from the time the funnel valve is opened until the liquid wicks into the product from the bottom of the dosing ring. Wait twenty minutes. During the twenty minute wait period after the first dose is applied, weigh a stack of filter papers (19–22 g, Whatman #3, 11.0 cm or equivalent, that have been exposed to room humidity for minimum of 2 hours before testing). The stack of preweighed filter papers are placed on the center of the wetted area. A cylindrical weight (8.9 cm diameter, 9.8 lb.) is placed on top of these filter papers. After two minutes the weight is removed, the filter papers are weighed and the weight change recorded. The procedure is repeated two more times. A second dose of synthetic urine is added to the diaper, and the acquisition time is determined, filter papers are placed on the sample for two minutes, and the weight change determined. For the second dose, the weight of the dry filter papers is 29–32 g, and for the third dose, the weight of the filter papers is 39–42 g. The dry papers from the prior dosage are supplemented with additional dry filter papers.

Liquid acquisition time is reported as the length of time (seconds) necessary for the liquid to be absorbed into the product for each of the three doses. The results are summarized in Table 2.

Rewet is reported as the amount of liquid (grams) absorbed back into the filter papers after each liquid dose (i.e., difference between the weight of wet filter papers and the weight of dry filter papers). The results are also summarized in Table 2.

TABLE 2

Acquisition Time and Rewet Comparison

| Composite | SAP % (w/w) | Basis Weight (gsm) | Acquisition Time (Sec) | | | Rewet (g) | | |
|---|---|---|---|---|---|---|---|---|
| | | | Insult 1 | Insult 2 | Insult 3 | Insult 1 | Insult 2 | Insult 3 |
| A1 | 45.0 | 668 | 20 | 16 | 18 | 0.1 | 0.2 | 0.5 |
| A2 | 39.3 | 665 | 19 | 16 | 19 | 0.1 | 0.2 | 0.5 |
| A3 | 37.0 | 715 | 26 | 16 | 17 | 0.1 | 0.2 | 0.5 |
| A4 | 46.0 | 710 | 18 | 16 | 24 | 0.1 | 0.1 | 0.3 |
| B1 | 49.4 | 568 | 16 | 19 | 26 | 0.1 | 0.4 | 2.4 |
| B2 | 38.3 | 648 | 17 | 19 | 22 | 0.1 | 0.7 | 2.5 |
| B3 | 35.9 | 687 | 29 | 26 | 27 | 0.2 | 0.2 | 0.7 |
| B4 | 38.8 | 672 | 17 | 18 | 21 | 0.1 | 0.3 | 0.9 |
| Commercial air-laid core | 40.0 | 625 | 34 | 35 | 39 | 0.1 | 4.0 | 12.6 |

As indicated in Table 2, the acquisition times for representative composites (Composites A1–A4) were significantly less than for the commercially available core.

The rewet of the representative composites (Composites A1–A4) is significantly less than for the other cores. While most of the composites exhibited relatively low rewet initially, after the third insult the commercially available core showed substantial rewet. In contrast, Composites A continued to exhibit low rewet.

Example 3

Horizontal and Vertical Wicking for a Representative Fluted Absorbent Composite

In this example, the wicking characteristics of a representative fluted absorbent composite (Composite A) are compared to a commercially available diaper storage core (Diaper B, Procter & Gamble) and a wet-laid storage core having absorbent material distributed uniformly throughout the composite (Composite B).

The horizontal wicking test measures the time required for liquid to horizontally wick preselected distances. The test is performed by placing a sample composite on a horizontal surface with one end in contact with a liquid bath and measuring the time required for liquid to wick preselected distances. Briefly, a sample composite strip (40 cm×10 cm) is cut from a pulp sheet or other source. If the sheet has a machine direction, the cut is made such that the 40 cm length of the strip is parallel to the machine direction. For absorbent composites, the strip is centered such that four bands of absorbent material are within the strip's width. Starting at one end of the 10 cm width of the strip mark a first line at 4.5 cm from the strip edge and then mark consecutive lines at 5 cm intervals along the entire length of the strip (i.e., 0 cm, 5 cm, 10 cm, 15 cm, 20 cm, 25 cm, 30 cm, and 35 cm). Prepare a horizontal wicking apparatus having a center trough with level horizontal wings extending away from opposing sides of the trough. The nonsupported edge of each wing being flush with the inside edge of the trough. On each wings' end place a plastic extension to support each wing in a level and horizontal position. The trough is then filled with synthetic urine. The sample composite strip is then gently bent at the 4.5 cm mark to form an approximately 45° angle in the strip. The strip is then placed on the wing such that the strip lays horizontally and the bent end of the strip extend into and contacts the liquid in the trough. Begin timing liquid wicking when the liquid reaches the first line marked on the composite 5 cm from the 4.5 cm bend. The wicking time is then recorded at 5 cm intervals when 50 percent of the liquid front reaches the marked interval (e.g., 5 cm, 10 cm). The liquid level in the trough is maintain at a relatively constant level throughout the test by replenishing with additional synthetic urine. The horizontal wicking results are summarized in Table 3.

TABLE 3

Horizontal Wicking Comparison

| Distance | Wicking Time (sec) | | |
|---|---|---|---|
| (cm) | Diaper B | Composite B | Composite A |
| 5 | 48 | 15 | 11 |
| 10 | 150 | 52 | 27 |
| 15 | 290 | 134 | 67 |
| 20 | 458 | 285 | 142 |
| 25 | 783 | 540 | 250 |
| 30 | 1703 | 1117 | 350 |
| 35 | — | 1425 | 480 |

The results tabulated above indicate that horizontal wicking is enhanced for the wet-laid composites compared to a conventional air-laid core. While the wicking time for Composite B is about 50 percent of that for the conventional diaper core, the wicking time for Composite A is about 50 percent of that for Composite B. Thus, the horizontal wicking for Composite A is about four times that of a commercially available storage core. Such a result indicates the effectiveness of the distribution zones of the composite created by the banded nature of the absorbent material.

The vertical wicking test measures the time required for liquid to vertically wick preselected distances. The test is performed by vertically suspending a sample composite with one end of the composite in contact with a liquid bath and measuring the time required for liquid to wick preselected distances. Prior to the test, sample composites (10 cm×22 cm) are cut and marked with consecutive lines 1 cm, 11 cm, 16 cm, and 21 cm from one of the strip's edges. Preferably, samples are preconditioned for 12 hours at 50 percent relative humidity and 23° C. and then stored in sample bags until testing. The sample composite is oriented lengthwise vertically and clamped from its top edge at the 1 cm mark and allowing its bottom edge to contact a bath containing synthetic urine. Timing commences once the strip is contacted with the liquid. The time required for 50 percent of the wicking front to reach 5 cm, 10 cm, 15 cm, and 20 cm is then recorded. The vertical wicking results are summarized in Table 4.

TABLE 4

Vertical Wicking Comparison

| Distance | Wicking Time (sec) | | |
|---|---|---|---|
| (cm) | Diaper B | Composite B | Composite A |
| 5 | 20 | 6 | 11 |
| 10 | Fell Apart | 54 | 51 |
| 15 | — | 513 | 257 |
| 20 | — | 3780 | 1110 |

As for the horizontal wicking results, wet-laid Composites A and B have significantly greater vertical wicking. Moreover, as between Composites A and B, the composite can distribute liquid remote from insult more rapidly than even for the wet-laid composite having absorbent material distributed uniformly throughout the composite. The results also show that the wet-laid composites have significantly greater wet tensile strength compared to the conventional air-laid composite.

Example 4

Liquid Distribution for a Representative Fluted Absorbent Composite

In this example, the distribution of liquid in a fluted absorbent composite (Composite A) is compared to that of two commercially available diapers (Diapers A and B above). The test measures the capacity of a diaper core to distribute acquired liquid. Perfect distribution would have 0% deviation from average. Ideal liquid distribution would result in equal distribution of the applied liquid in each of the four distribution zones (i.e., about 25% liquid in each zone).

Liquid distribution is determined by weighing different zones of a sample that has been subjected to the multiple-dose rewet test described above in Example 2. Basically, after the last rewet, the wings of the diaper are removed and then cut into four equal length distribution zones. Each zone is then weighed to determine the weight of liquid contained in each zone.

The liquid distribution results for representative fluted absorbent composites approach ideality. The results indicate that while the representative commercial storage cores accumulate liquid near the site of insult, liquid is efficiently and effectively distributed throughout the fluted absorbent storage core.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for making a fibrous layer, comprising:
refining cellulosic fibers to provide refined fibers, wherein the cellulosic fibers comprise crosslinked cellulosic fibers;
combining the refined fibers with a dispersion medium to provide a fibrous slurry;
depositing the fibrous slurry on a foraminous support to provide a wet composite;
introducing an absorbent material into said wet composite at a plurality of points across the width of the composite in the cross-machine direction, said absorbent material having an absorbent capacity greater than the refined cellulosic fibers; and
drying the wet composite to provide a fibrous layer.

2. The method of claim 1, wherein the cellulosic fibers comprise a blend of crosslinked cellulosic fibers and non-crosslinked cellulosic fibers.

3. The method of claim 2, wherein the noncrosslinked fibers are at least one of softwood fibers or hardwood fibers.

4. The method of claim 2, wherein the noncrosslinked fibers comprise southern pine fibers.

5. The method of claim 1, wherein the cellulosic fibers comprise a blend of crosslinked cellulosic fibers and southern pine fibers.

6. The method of claim 1, wherein the cellulosic fibers comprise a refined blend of said crosslinked cellulosic fibers and southern pine fibers.

7. The method of claim 1, wherein the cellulosic fibers comprise a blend of crosslinked cellulosic fibers and refined southern pine fibers.

8. The method of claim 1, wherein the cellulosic fibers comprise a refined blend of crosslinked cellulosic fibers and refined southern pine fibers.

9. The method of claim 1, wherein the method is carried out on at least one of a Fourdrinier or a twin-wire paper-making machine.

10. The method of claim 1, wherein the method is at least one of a wetlaid method and a foam-forming method.

11. A method for making a fibrous layer, comprising:
refining cellulosic fibers to provide refined fibers, wherein the cellulosic fibers comprise crosslinked cellulosic fibers;
combining the refined fibers with a dispersion medium to provide a fibrous slurry;
moving a first foraminous element in a first path;
moving a second foraminous element in a second path;
passing a first portion of the fibrous slurry into contact with the first foraminous element;
passing a second portion of the fibrous slurry into contact with the second foraminous element;
forming a fibrous web from the slurry by withdrawing liquid from the slurry through the first and second foraminous elements;
introducing and absorbent material into said fibrous web at a plurality of points across the width of the composite in the cross-machine direction, said absorbent material having an absorbant capacity greater than the refined cellulosic fibers; and
drying the web provide a fibrous layer.

12. The method of claim 11, wherein the cellulosic fibers comprise a blend of crosslinked cellulosic fibers and non-crosslinked cellulosic fibers.

13. The method of claim 12, wherein the noncrosslinked fibers are at least one of softwood fibers or hardwood fibers.

14. The method of claim 12, wherein the noncrosslinked fibers comprise southern pine fibers.

15. The method of claim 11, wherein the cellulosic fibers comprise a blend of crosslinked cellulosic fibers and southern pine fibers.

16. The method of claim 11, wherein the cellulosic fibers comprise a refined blend of said crosslinked cellulosic fibers and southern pine fibers.

17. The method of claim 11, wherein the cellulosic fibers comprise a blend of crosslinked cellulosic fibers and refined southern pine fibers.

18. The method of claim 11, wherein the cellulosic fibers comprise a refined blend of crosslinked cellulosic fibers and refined southern pine fibers.

19. The method of claim 11, wherein the method is at least one of a wetlaid method or a foam-forming method.

* * * * *